United States Patent
Vazquez et al.

(10) Patent No.: US 10,981,921 B2
(45) Date of Patent: *Apr. 20, 2021

(54) FRAGMENT SYNTHESIS OF SUBSTITUTED CYCLIC PEPTIDES

(71) Applicants: Zealand Pharma A/S, Søborg (DK); Universite de Montreal, Montreal (CA)

(72) Inventors: Manuel Perez Vazquez, Milton (CA); M. Monzur Morshed, Mississauga (CA); Jennifer L. Hickey, Toronto (CA); Marc-André Poupart, Laval (CA); Gaoqiang Yang, Montreal (CA); James Gillard, Rosemere (CA); Adam Paul Kafal, Toronto (CA); Andrew L. Roughton, Port Hope (CA)

(73) Assignee: Zealand Pharma A/S, Søborg (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/985,096

(22) Filed: Aug. 4, 2020

(65) Prior Publication Data

US 2020/0361944 A1 Nov. 19, 2020

Related U.S. Application Data

(63) Continuation of application No. 15/775,319, filed as application No. PCT/CA2016/000275 on Nov. 14, 2016.

(60) Provisional application No. 62/254,003, filed on Nov. 11, 2015.

(51) Int. Cl.
| | |
|---|---|
| C07C 231/02 | (2006.01) |
| C07D 487/04 | (2006.01) |
| C07C 271/18 | (2006.01) |
| C07C 271/22 | (2006.01) |
| C07D 207/16 | (2006.01) |
| C07K 7/06 | (2006.01) |
| C07K 7/56 | (2006.01) |
| C07K 1/107 | (2006.01) |
| A61P 1/04 | (2006.01) |
| C07K 7/54 | (2006.01) |
| C07K 7/64 | (2006.01) |
| A61K 9/00 | (2006.01) |
| A61K 38/00 | (2006.01) |

(52) U.S. Cl.
CPC .............. *C07D 487/04* (2013.01); *A61P 1/04* (2018.01); *C07C 271/18* (2013.01); *C07C 271/22* (2013.01); *C07D 207/16* (2013.01); *C07K 1/1075* (2013.01); *C07K 7/06* (2013.01); *C07K 7/54* (2013.01); *C07K 7/56* (2013.01); *C07K 7/64* (2013.01); *A61K 9/0014* (2013.01); *A61K 9/0053* (2013.01); *A61K 38/00* (2013.01); *C07C 2603/18* (2017.05)

(58) Field of Classification Search
CPC .................................................... C07C 231/02

USPC ........................................................ 564/138
See application file for complete search history.

(56) References Cited

U.S. PATENT DOCUMENTS

| | | |
|---|---|---|
| 5,296,604 A | 3/1994 | Hanko et al. |
| 5,693,325 A | 12/1997 | Kahn |
| 5,693,612 A | 12/1997 | Jonczyk et al. |
| 5,693,750 A | 12/1997 | Ohki et al. |
| 5,696,084 A | 12/1997 | Lartey et al. |
| 5,705,481 A | 1/1998 | Jonczyk et al. |
| 5,731,286 A | 3/1998 | Harbeson et al. |
| 6,492,553 B1 | 12/2002 | Hulme et al. |
| 2008/0200398 A1 | 8/2008 | Smyth et al. |
| 2011/0251247 A1 | 10/2011 | Chubb et al. |
| 2014/0193465 A1 | 7/2014 | Bhandari et al. |
| 2019/0077805 A1 | 3/2019 | Vazquez et al. |
| 2020/0165300 A1 | 5/2020 | Vazquez et al. |

FOREIGN PATENT DOCUMENTS

| | | |
|---|---|---|
| CA | 2427046 A1 | 11/2003 |
| DE | 3219113 A1 | 11/1983 |
| WO | WO-96/20216 A1 | 7/1996 |
| WO | WO-2001/010799 A1 | 2/2001 |
| WO | WO-02/066500 A2 | 8/2002 |
| WO | WO-2008/046232 A1 | 4/2008 |
| WO | WO-2009/141687 A1 | 11/2009 |
| WO | WO-2010/105363 A1 | 9/2010 |
| WO | WO-2010/107832 A1 | 9/2010 |
| WO | WO-2014/059213 A1 | 4/2014 |
| WO | WO-2016/054411 A1 | 4/2016 |
| WO | WO-2016/054445 A1 | 4/2016 |
| WO | WO-2017/079820 A1 | 5/2017 |
| WO | WO-2017/079821 A1 | 5/2017 |

OTHER PUBLICATIONS

Achmatowicz et al., The synthesis of L-proline derived hexaazamacrocyclic ligands of C3 symmetry via intramolecular methyl ester aminolysis, Tetrahedron: Asymmetry 12 (2001) 487-495.

Baktharaman et al., "Amino carbonyl compounds in organic synthesis," Aldrichimica Acta, 41:109-117 (2008).

Burden et al., "Synthesis and biological activities of YkFA analogues: effects of position 4 substitutions and altered ring size on in vitro opioid activity," Bioorg Med Chem Lett. 12(2):213-6 (2002).

(Continued)

*Primary Examiner* — Douglas M Willis
(74) *Attorney, Agent, or Firm* — Clark & Elbing LLP

(57) ABSTRACT

There is described herein use of a compound of formula (I) below to make cyclic peptides.

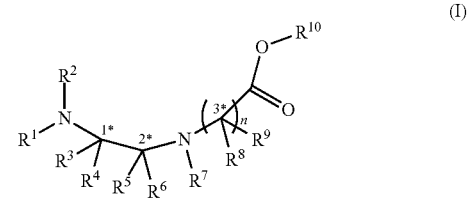

(I)

12 Claims, 2 Drawing Sheets

(56) References Cited

OTHER PUBLICATIONS

Chen et al., "Synthesis of 12-membered macrocyclic templates and library analogs for PPI," Tetrahedron Letters. 54(25):3298-301 (2013).
Couturier et al., "Aziridinium from N,N-dibenzyl serine methyl ester: synthesis of enantiomerically pure beta-amino and alpha,beta-diamino esters," Org Lett. 8(10):2183-6 (2006).
Dutta et al., "Potent cyclic monomeric and dimeric peptide inhibitors of VLA-4 (α4β1 integrin)-mediated cell adhesion based on the Ile-Leu-Asp-Val tetrapeptide," J Pept Sci. 6(7):321-41 (2000).
Dörwald, F. Zaragoza. Side Reactions in Organic Synthesis: A Guide to Successful Synthesis Design, Weinheim: Wiley-VCH Verlag GmbH & Co. KGaA, 2005, Preface.
Extended European Search Report for European Application No. 16863253.7, dated Oct. 17, 2019 (6 pages).
Greene et al., "Preface to the Third Edition," *Protective Groups in Organic Synthesis*, Third Edition. John Wiley & Sons, Inc., v-vi (1999) (6 pages).
Hili et al., "Macrocyclization of linear peptides enabled by amphoteric molecules," J Am Chem Soc. 132(9):2889-91 (2010).
Hili et al., "Readily available unprotected amino aldehydes," J Am Chem Soc. 128(46):14772-3 (2006).
Hirose et al., "Total synthesis and determination of the absolute configuration of guadinomines B and C2," Chemistry 14(27):8220-38 (2008).
International Search Report and Written Opinion Issued in Corresponding PCT Application No. PCT/CA2016/000274, dated Dec. 19, 2016.
International Search Report and Written Opinion Issued in Corresponding PCT Application No. PCT/CA2016/000275, dated Feb. 28, 2017.
International Search Report and Written Opinion Issued in Corresponding PCT Application No. PCT/CA2017/000244, dated Feb. 8, 2018.
International Search Report and Written Opinion Issued in PCT Application No. PCT/CA2018/000087, dated Aug. 7, 2018 (7 pages).
Mohan et al., "Synthesis and biological activity of angiotensin II analogues containing a Val-His replacement, Val psi[CH(CONH2)NH]His," J Med Chem. 34(8):2402-10 (1991).
Murray et al., "The synthesis of cyclic tetrapeptoid analogues of the antiprotozoal natural product apicidin," Bioorg Med Chem Lett. 11(6):773-6 (2001).
Naveh et al., "Developing potent backbone cyclic peptides bearing the shared epitope sequence as rheumatoid arthritis drug-leads," Bioorg Med Chem Lett. 22(1):493-6 (2012).
Patil et al., "Second generation, arginine-rich (R-X'-R)(4)-type cell-penetrating a-ω-a-peptides with constrained, chiral ω-amino acids (X') for enhanced cargo delivery into cells," Bioorg Med Chem Lett. 24(17):4198-202 (2014).
Pil et al., "Synthesis and electrophysiological characterization of cyclic morphiceptin analogues," Biochem Pharmacol. 67(10):1887-95 (2004).
Quartara et al., "Influence of lipophilicity on the biological activity of cyclic pseudopeptide NK-2 receptor antagonist," J Med Chem. 37(21):3630-8 (1994).
Rotstein et al., "Synthesis of peptide macrocycles using unprotected amino aldehydes," Nat Protoc. 5(11):1813-22 (2010).
Slama et al., "Convenient Synthesis of 1,2-Diamines from β-Chloro Amines: Precursors of New Substituted Piperazin-2-ones" Synthetic Communications, 43(17):2286-2293, 2013.
Suarez-Gea et al., "General Method for the Synthesis of Carbamoylmethyleneamino Pseudopeptides" Journal of Organic Chemistry, 59(13):3600-3603, 1994.
Supporting Information for Patil et al., "Second generation, arginine-rich (R-X'-R)(4)-type cell-penetrating alpha-omega-alpha-peptides with constrained, chiral omega-amino acids (X') for enhanced cargo delivery into cells," Bioorg Med Chem Lett. 24(17):4198-202 (2014).
Tal-Gan et al., "Backbone cyclic peptide inhibitors of protein kinase B (PKB/Akt)," J Med Chem. 54(14):5154-64 (2011).
Tamamura et al., "Stereoselective synthesis of [L-Arg-L/D-3-(2-naphthyl)alanine]-type (E)-alkene dipeptide isosteres and its application to the synthesis and biological evaluation of pseudopeptide analogues of the CXCR4 antagonist FC131," J Med Chem. 48(2):380-91 (2005).
Treder et al., "Solid-phase synthesis of piperazinones via disrupted Ugi condensation," Org Lett. 16(17):4674-7 (2014).
Vercillo et al., "Design and synthesis of cyclic RGD pentapeptoids by consecutive Ugi reactions," Org Lett. 10(2):205-8 (2008).
Verheijen et al., "An expeditious liquid-phase synthesis of cyclic peptide nucleic acids," Tetrahedron Letters. 41(20):3991-5 (2000).
Wagner et al., "New naturally occurring amino acids," Angew Chem Int Ed Engl. 22(11):816-28 (1983).
Yudin et al., "Overcoming the demons of protecting groups with amphoteric molecules," Chemistry 13(23):6538-42 (2007).
Boer et al., "Design and synthesis of potent and selective alpha(4)beta(7) integrin antagonists," J Med Chem. 44(16):2586-92 (2001).
Examination Report for Indian Application No. 201817021544, dated May 18, 2020 (6 pages).
Extended European Search Report for European Application No. 17870529.9, dated Jul. 28, 2020 (14 pages).
Partial Supplementary European Search Report for European Application No. 17870529.9, dated Apr. 23, 2020 (10 pages).

FRAGMENT SYNTHESIS OF SUBSTITUTED CYCLIC PEPTIDES

FIELD

The present invention relates to cyclic amino acid molecules and methods of preparing the same.

BACKGROUND

Peptides play vital roles by mediating a wide range of biological processes, acting as hormones, antibiotics, and signaling molecules. Due to the highly specific interaction with their biological targets, peptides have been widely used in medicine. However, the enormous therapeutic potential of peptides is not always easy to realize due to their low bioavailability. This shortcoming is a consequence of the degradation of peptides by endo- and exopeptidases, which results in poor in vivo stability of peptides. Compared to their linear counterparts, cyclic peptides are more resistant to degradation. There are two main reasons for this stability. Firstly, exopeptidases cannot cleave the cyclic peptide at its (non-existent) ends. Secondly, cyclic peptides, especially those with a small-to-medium ring size, are protected against endopeptidases because the constrained cyclic peptide backbone prevents the adaptation of the required extended conformation during proteolysis. In addition, the reduced charge and intramolecular hydrogen bonding within cyclic peptides facilitate passive membrane permeability, which contributes to their enhanced bioavailability. Most significantly, conformational constraints imposed on the amino acid sequence by the cyclic topology maximize enthalpic interactions between cyclic peptides and their biochemical targets while ensuring favourable entropy of binding.

SUMMARY OF THE INVENTION

In an aspect, there is provided a compound of formula (I):

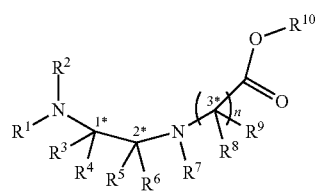

(I)

wherein $R^1$, $R^2$, $R^3$, $R^4$, $R^5$ and $R^6$ are each independently selected from the group consisting of a protecting group; H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH2C(O)R, wherein R is selected from —OH, lower alkyl, aryl, -loweralkyl-aryl, or —NRaRb, where Ra and Rb are independently selected from H, lower alkyl, aryl or -loweralkyl-aryl; —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;

provided that $R^3$ or $R^4$ can be covalently linked to $R^1$ or $R^2$ to form a cyclic secondary amine, and/or to $R^5$ or $R^6$ to form a ring; $R^3$ and $R^4$ may be covalently linked to each other to form a ring; and $R^5$ and $R^6$ may be covalently bound to each other to form a ring;

$R^7$ is H, a protecting group, lower alkyl, benzyl, alkenyl, lower alkyloxy, aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH2C(O)R; —C(O)Rc; all of which are optionally substituted at one or more substitutable positions with one or more suitable substituents or along with $R^8$ or $R^9$, a cyclic side chain of a proteinogenic or a non-proteinogenic amino acid having, the N-terminus thereof being the N—$R^7$, wherein the proteinogenic or a non-proteinogenic amino acid can be substituted with a suitable substituent;

$R^8$ and $R^9$ are independently selected from the amino acid side chains of a proteinogenic or a non-proteinogenic amino acid having, the N-terminus thereof being the N—$R^7$, or may form a cyclic side chain with $R^7$; and $R^{10}$ is H, a protecting group, a resin, lower alkyl, allyl, tert-butyl, or benzyl;

stereocentres 1*, 2* and 3* are each independently selected from R and S; and n is 1, 2, 3, or 4 and where n is 2-4, each $R^8$ and each $R^9$ are independent of each other.

In an aspect, there is provided a method of preparing the compound of any one of claims 1-9, comprising reacting

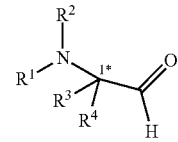

with

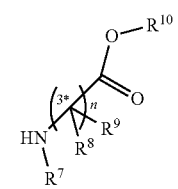

and an isocyanide; wherein $R^5$ or $R^6$ is a carboxamide.

In an aspect, there is provided a method of preparing the compound of formula (II),

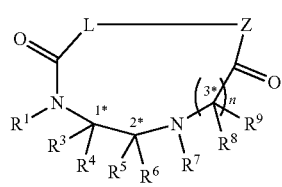

(II)

comprising binding at least one amino acid to the compound of any one of claims 1-9 (Formula (I)) using protecting group based peptide synthesis and performing a head-to-tail cyclization;

wherein Z is an amino terminus of an amino acid; —C=O— adjacent L is the carboxy terminus of an amino acid; and Z along with L and —C=O— is a proteogenic or non-proteogenic amino acid or peptide or peptidomimetic In an aspect, there is provided a method of preparing the compound of formula (III),

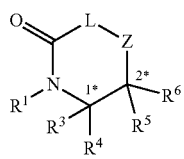
(III)

comprising performing a head-to-tail cyclization on the compound of any one of claims 1-9;
wherein $R^1$, $R^3$, $R^4$, $R^5$ and $R^6$ are each independently selected from the group consisting of H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH$_2$C(O)R, wherein R is selected from —OH, lower alkyl, aryl, -loweralkyl-aryl, or —NRaRb, where Ra and Rb are independently selected from H, lower alkyl, aryl or -loweralkyl-aryl; —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;
provided that $R^3$ or $R^4$ can be covalently linked to $R^1$ to form a cyclic secondary amine, and/or to $R^5$ or $R^6$ to form a ring; $R^3$ and $R^4$ may be covalently linked to each other to form a ring; and $R^5$ and $R^6$ may be covalently bound to each other to form a ring;
stereocentres 1* and 2* and 3* are independently selected from R and S; and
Z-L-C=O is an amino acid.

In an aspect, there is provided a compound of formula (II)

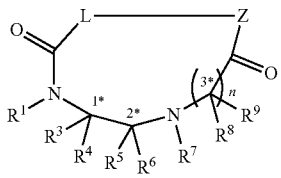
(II)

wherein
$R^1$, $R^2$, $R^3$, $R^4$, $R^5$ and $R^6$ are each independently selected from the group consisting of a protecting group; H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH$_2$C(O)R, wherein R is selected from —OH, lower alkyl, aryl, -loweralkyl-aryl, or —NRaRb, where Ra and Rb are independently selected from H, lower alkyl, aryl or -loweralkyl-aryl; —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;
provided that $R^3$ or $R^4$ can be covalently linked to $R^1$ or $R^2$ to form a cyclic secondary amine, and/or to $R^5$ or $R^6$ to form a ring; $R^3$ and $R^4$ may be covalently bound to each other to form a ring; and $R^5$ and $R^6$ may be covalently bound to each other to form a ring;
$R^7$ is H, a protecting group, lower alkyl, benzyl, alkenyl, lower alkyloxy; aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH$_2$C(O)R; —C(O)Rc; all of which are optionally substituted at one or more substitutable positions with one or more suitable substituents;
or, along with $R^8$ or $R^9$, a cyclic side chain of a proteinogenic or a non-proteinogenic alpha-amino acid having, the N-terminus thereof being the N—$R^7$;
$R^8$ and $R^9$ are independently selected from the amino acid side chains of a proteinogenic or a non-proteinogenic alpha-amino acid having, the N-terminus thereof being the N—$R^7$, or may form a cyclic side chain with $R^7$;
stereocentres 1*, 2* and 3* are each independently selected from R and S;
wherein Z is an amino terminus of an amino acid; —C=O— adjacent L is the carboxy terminus of an amino acid; and Z along with L and —C=O— is a proteogenic or non-proteogenic amino acid or peptide or peptidomimetic; and
n is 1, 2, 3, or 4 and where n is 2-4, each $R^8$ and each $R^9$ are independent of each other.

In an aspect, there is provided a compound of formula (III),

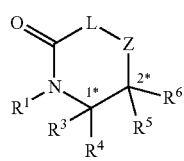
(III)

wherein $R^1$, $R^3$, $R^4$, $R^5$ and $R^6$ are each independently selected from the group consisting of H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH$_2$C(O)R, wherein R is selected from —OH, lower alkyl, aryl, -loweralkyl-aryl, or —NRaRb, where Ra and Rb are independently selected from H, lower alkyl, aryl or -loweralkyl-aryl; —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;
provided that $R^3$ or $R^4$ can be covalently linked to $R^1$ to form a cyclic secondary amine, and/or to $R^5$ or $R^6$ to form a ring; $R^3$ and $R^4$ may be covalently bound to each other to form a ring; and $R^5$ and $R^6$ may be covalently bound to each other to form a ring;
stereocentres 1* and 2* and 3* are independently selected from R and S; and
Z-L-C=O is an amino acid.

DETAILED DESCRIPTION

Figures 1A, 1B:
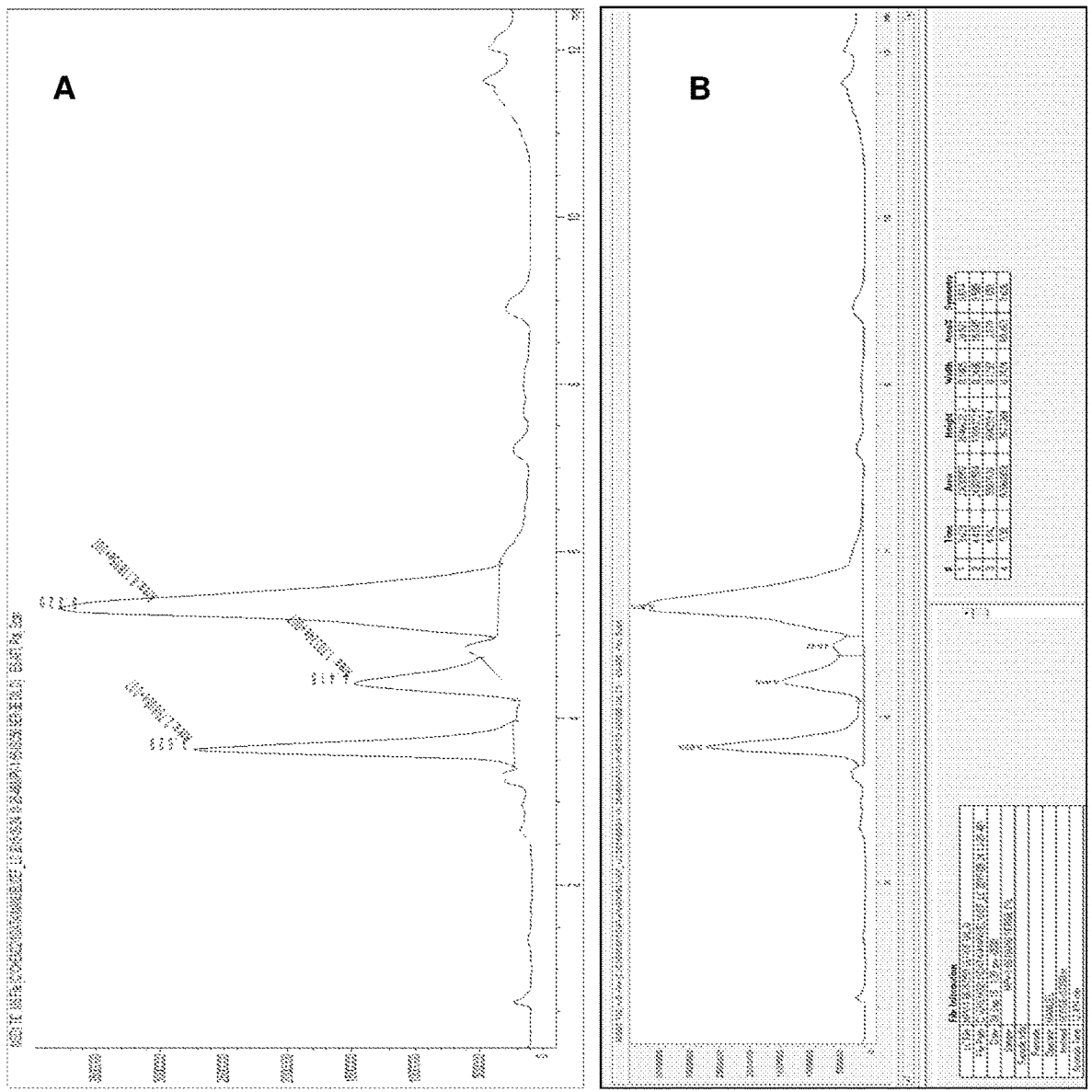
FIG. 1a is an HPLC trace of a Ugi reaction conducted at 0° C. in dichloromethane and methanol with no Bronsted or Lewis acid.
FIG. 1b is an HPLC trace of a Ugi reaction conducted at 0° C. in dichloromethane and methanol with no Bronsted or Lewis acid.

In an aspect, there is provided a compound of formula (I):

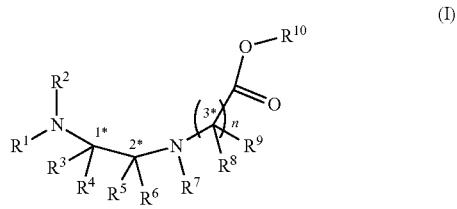

(I)

wherein $R^1$, $R^2$, $R^3$, $R^4$, $R^5$ and $R^6$ are each independently selected from the group consisting of a protecting group; H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH2C(O)R, wherein R is selected from —OH, lower alkyl, aryl, -loweralkyl-aryl, or —NRaRb, where Ra and Rb are independently selected from H, lower alkyl, aryl or -loweralkyl-aryl; —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;

provided that $R^3$ or $R^4$ can be covalently linked to $R^1$ or $R^2$ to form a cyclic secondary amine, and/or to $R^5$ or $R^6$ to form a ring; $R^3$ and $R^4$ may be covalently linked to each other to form a ring; and $R^5$ and $R^6$ may be covalently bound to each other to form a ring;

$R^7$ is H, a protecting group, lower alkyl, benzyl, alkenyl, lower alkyloxy; aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH$_2$C(O)R; —C(O)Rc; all of which are optionally substituted at one or more substitutable positions with one or more suitable substituents or along with $R^8$ or $R^9$, a cyclic side chain of a proteinogenic or a non-proteinogenic amino acid having, the N-terminus thereof being the N—$R^7$, wherein the proteinogenic or a non-proteinogenic amino acid can be substituted with a suitable substituent;

$R^8$ and $R^9$ are independently selected from the amino acid side chains of a proteinogenic or a non-proteinogenic amino acid having, the N-terminus thereof being the N—$R^7$, or may form a cyclic side chain with $R^7$; and $R^{10}$ is H, a protecting group, a resin, lower alkyl, allyl, tert-butyl, or benzyl;

stereocentres 1*, 2* and 3* are each independently selected from R and S; and n is 1, 2, 3, or 4 and where n is 2-4, each $R^8$ and each $R^9$ are independent of each other.

A protecting group or protective group is a substituent introduced into a molecule to obtain chemoselectivity in a subsequent chemical reaction. Many protecting groups are known in the art and a skilled person would understand the kinds of protecting groups that would be incorporated and could be used in connection with the methods described herein. In "protecting group based peptide synthesis", typically solid phase peptide synthesis, the desired peptide is prepared by the step-wise addition of amino acid moieties to a building peptide chain. The two most widely used protocols, in solid-phase synthesis, employ tert-butyloxycarbonyl (Boc) or 9-fluorenylmethoxycarbonyl (Fmoc) as amino protecting groups.

Amino protecting groups generally protect an amino group against undesirable reactions during synthetic procedures and which can later be removed to reveal the amine. Commonly used amino protecting groups are disclosed in Greene, T. W. et al., Protective Groups in Organic Synthesis, 3rd Edition, John Wiley & Sons (1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, .alpha.-.alpha.-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

As used herein, the term "amino acid" refers to molecules containing an amine group, a carboxylic acid group and a side chain that varies. Amino acid is meant to include not only the twenty amino acids commonly found in proteins but also non-standard amino acids and unnatural amino acid derivatives known to those of skill in the art, and therefore includes, but is not limited to, alpha, beta and gamma amino acids. Peptides are polymers of at least two amino acids and may include standard, non-standard, and unnatural amino acids.

The term "suitable substituent" as used in the context of the present invention is meant to include independently H; hydroxyl; cyano; alkyl, such as lower alkyl, such as methyl, ethyl, propyl, n-butyl, t-butyl, hexyl and the like; alkoxy, such as lower alkoxy such as methoxy, ethoxy, and the like; aryloxy, such as phenoxy and the like; vinyl; alkenyl, such as hexenyl and the like; alkynyl; formyl; haloalkyl, such as lower haloalkyl which includes $CF_3$, $CCl_3$ and the like; halide; aryl, such as phenyl and napthyl; heteroaryl, such as thienyl and furanyl and the like; amide such as $C(O)NR_aR_b$, where $R_a$ and $R_b$ are independently selected from lower alkyl, aryl or benzyl, and the like; acyl, such as $C(O)$—$C_6H_5$, and the like; ester such as —$C(O)OCH_3$ the like; ethers and thioethers, such as O-Bn and the like; thioalkoxy; phosphino; and —$NR_aR_b$, where $R_a$ and $R_b$ are independently selected from lower alkyl, aryl or benzyl, and the like. It is to be understood that a suitable substituent as used in the context of the present invention is meant to denote a substituent that does not interfere with the formation of the desired product by the processes of the present invention.

As used in the context of the present invention, the term "lower alkyl" as used herein either alone or in combination with another substituent means acyclic, straight or branched chain alkyl substituent containing from one to six carbons and includes for example, methyl, ethyl, 1-methylethyl, 1-methylpropyl, 2-methylpropyl, and the like. A similar use of the term is to be understood for "lower alkoxy", "lower thioalkyl", "lower alkenyl" and the like in respect of the number of carbon atoms. For example, "lower alkoxy" as used herein includes methoxy, ethoxy, t-butoxy.

The term "alkyl" encompasses lower alkyl, and also includes alkyl groups having more than six carbon atoms, such as, for example, acyclic, straight or branched chain alkyl substituents having seven to ten carbon atoms.

The term "aryl" as used herein, either alone or in combination with another substituent, means an aromatic monocyclic system or an aromatic polycyclic system. For example, the term "aryl" includes a phenyl or a napthyl ring, and may also include larger aromatic polycyclic systems, such as fluorescent (eg. anthracene) or radioactive labels and their derivatives.

The term "heteroaryl" as used herein, either alone or in combination with another substituent means a 5, 6, or 7-membered unsaturated heterocycle containing from one to 4 heteroatoms selected from nitrogen, oxygen, and sulphur and which form an aromatic system. The term "heteroaryl" also includes a polycyclic aromatic system comprising a 5, 6, or 7-membered unsaturated heterocycle containing from one to 4 heteroatoms selected from nitrogen, oxygen, and sulphur.

The term "cycloalkyl" as used herein, either alone or in combination with another substituent, means a cycloalkyl substituent that includes for example, but is not limited to, cyclopropyl, cyclobutyl, cyclopentyl, cyclohexyl and cycloheptyl.

The term "cycloalkyl-alkyl-" as used herein means an alkyl radical to which a cycloalkyl radical is directly linked; and includes, but is not limited to, cyclopropylmethyl, cyclobutylmethyl, cyclopentylmethyl, 1-cyclopentylethyl, 2-cyclopentylethyl, cyclohexylmethyl, 1-cyclohexylethyl and 2-cyclohexylethyl. A similar use of the "alkyl" or "lower alkyl" terms is to be understood for aryl-alkyl-, aryl-lower-alkyl- (eg. benzyl), -lower alkyl-alkenyl (eg. allyl), heteroaryl-alkyl-, and the like as used herein. For example, the term "aryl-alkyl-" means an alkyl radical, to which an aryl is bonded. Examples of aryl-alkyl- include, but are not limited to, benzyl (phenylmethyl), 1-phenylethyl, 2-phenylethyl and phenylpropyl.

As used herein, the term "heterocycle", either alone or in combination with another radical, means a monovalent radical derived by removal of a hydrogen from a three- to seven-membered saturated or unsaturated (including aromatic) cyclic compound containing from one to four heteroatoms selected from nitrogen, oxygen and sulfur. Examples of such heterocycles include, but are not limited to, aziridine, epoxide, azetidine, pyrrolidine, tetrahydrofuran, thiazolidine, pyrrole, thiophene, hydantoin, diazepine, imidazole, isoxazole, thiazole, tetrazole, piperidine, piperazine, homopiperidine, homopiperazine, 1,4-dioxane, 4-morpholine, 4-thiomorpholine, pyridine, pyridine-N-oxide or pyrimidine, and the like.

The term "alkenyl", as used herein, either alone or in combination with another radical, is intended to mean an unsaturated, acyclic straight chain radical containing two or more carbon atoms, at least two of which are bonded to each other by a double bond. Examples of such radicals include, but are not limited to, ethenyl (vinyl), 1-propenyl, 2-propenyl, and 1-butenyl.

The term "alkynyl", as used herein is intended to mean an unsaturated, acyclic straight chain radical containing two or more carbon atoms, at least two of which are bonded to each other by a triple bond. Examples of such radicals include, but are not limited to, ethynyl, 1-propynyl, 2-propynyl, and 1-butynyl.

The term "alkoxy" as used herein, either alone or in combination with another radical, means the radical —O—$(C_{1-n})$alkyl wherein alkyl is as defined above containing 1 or more carbon atoms, and includes for example methoxy, ethoxy, propoxy, 1-methylethoxy, butoxy and 1,1-dimethylethoxy. Where n is 1 to 6, the term "lower alkoxy" applies, as noted above, whereas the term "alkoxy" encompasses "lower alkoxy" as well as alkoxy groups where n is greater than 6 (for example, n=7 to 10). The term "aryloxy" as used herein alone or in combination with another radical means —O-aryl, wherein aryl is defined as noted above.

A peptide is a polymer of two or more amino acids.

In some embodiments, one and only one of $R^1$ and $R^2$ is a protecting group.

In some embodiments, $R^1$ and $R^2$ are both H.

In some embodiments, $R^3$ and $R^4$ are each independently selected from the group consisting of amino acid chains of a proteinogenic or a non-proteinogenic alpha-amino acids, preferably $CH_3$, H, isobutyl, and —CH2-S—R***, wherein R* is selected from lower alkyl; lower amino alkyl; aryl; heteroaryl; alkenyl; or, heterocycle; all of which are optionally substituted at one or more substitutable positions with one or more suitable substituents; preferably R*** is phenyl or phenyl substituted with lower alkyl, halogen, or lower amino alkyl. In some embodiments, the proteinogenic or non-proteinogenic alpha-amino acid is a primary amino acid. In some embodiments, the proteinogenic or non-proteinogenic alpha-amino acid is a secondary amino acid, preferably proline.

In some embodiments, $R^5$ and $R^6$ are either (i) H and a carboxamide, the carboxamide preferably being —C(O)NH-tert-butyl; or (ii) H and H respectively.

In some embodiments, $R^7$ and either $R^8$ or $R^9$ are selected to form proline, the N-terminus thereof being the N—$R^7$.

In some embodiments, $R^{10}$ is selected from the group consisting of $CH_3$ and H.

In some embodiments, none of $R^1$, $R^2$, $R^3$, $R^4$, $R^5$ and $R^6$ are an acid of the formula —C(O)OH.

In some embodiments, $R^7$ is H, a protecting group, lower alkyl, benzyl, or alkenyl.

In an aspect, there is provided a method of preparing the compound of any one of claims 1-9, comprising reacting

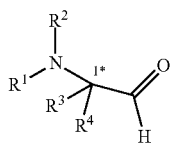

with

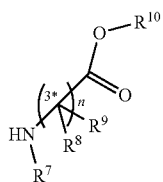

and an isocyanide; wherein $R^5$ or $R^6$ is a carboxamide.

In some embodiments, this method is performed in the presence of at least one of:

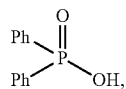

$CH_2Cl_2$, MeOH, or HCl.

In an aspect, there is provided a method of preparing the compound of formula (II),

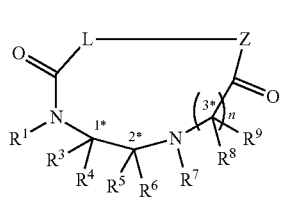

(II)

comprising binding at least one amino acid to the compound of any one of claims 1-9 (Formula (I)) using protecting group based peptide synthesis and performing a head-to-tail cyclization;

wherein Z is an amino terminus of an amino acid; —C=O— adjacent L is the carboxy terminus of an amino acid; and Z along with L and —C=O— is a proteogenic or non-proteogenic amino acid or peptide or peptidomimetic In some embodiments, the peptide is bound to the compound of Formula (I).

In some embodiments, the peptide is 2-8 amino acids in length.

In some embodiments, two or more fragment compounds described herein are bound to each other using the protecting group based peptide synthesis.

In an aspect, there is provided a method of preparing the compound of formula (III),

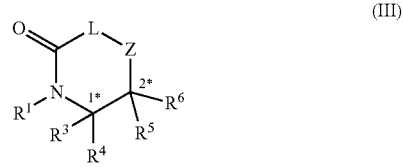

(III)

comprising performing a head-to-tail cyclization on the compound of any one of claims 1-9;

wherein $R^1$, $R^3$, $R^4$, $R^5$ and $R^6$ are each independently selected from the group consisting of H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH₂C(O)R, wherein R is selected from —OH, lower alkyl, aryl, -loweralkyl-aryl, or —NRaRb, where Ra and Rb are independently selected from H, lower alkyl, aryl or -loweralkyl-aryl; —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;

provided that $R^3$ or $R^4$ can be covalently linked to $R^1$ to form a cyclic secondary amine, and/or to $R^5$ or $R^6$ to form a ring; $R^3$ and $R^4$ may be covalently linked to each other to form a ring; and $R^5$ and $R^6$ may be covalently bound to each other to form a ring;

stereocentres 1* and 2* and 3* are independently selected from R and S; and

Z-L-C=O is an amino acid.

In some embodiments of the methods of preparing the compound of formulas (II) and (III), the protecting group based peptide synthesis is performed on solid phase. In some embodiments, the fragment compound described herein is bound to the solid phase.

In an aspect, there is provided a compound of formula (II)

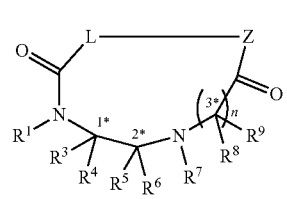

(II)

wherein $R^1$, $R^2$, $R^3$, $R^4$, $R^5$ and $R^6$ are each independently selected from the group consisting of a protecting group; H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH₂C(O)R, wherein R is selected from —OH, lower alkyl, aryl, -loweralkyl-aryl, or —NRaRb, where Ra and Rb are independently selected from H, lower alkyl, aryl or -loweralkyl-aryl; —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;

provided that $R^3$ or $R^4$ can be covalently linked to $R^1$ or $R^2$ to form a cyclic secondary amine, and/or to $R^5$ or $R^6$ to form a ring; $R^3$ and $R^4$ may be covalently bound to each other to form a ring; and $R^5$ and $R^6$ may be covalently bound to each other to form a ring;

$R^7$ is H, a protecting group, lower alkyl, benzyl, alkenyl, lower alkyloxy; aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH$_2$C(O)R; —C(O)Rc; all of which are optionally substituted at one or more substitutable positions with one or more suitable substituents or, along with $R^8$ or $R^9$, a cyclic side chain of a proteinogenic or a non-proteinogenic alpha-amino acid having, the N-terminus thereof being the N—$R^7$;

$R^8$ and $R^9$ are independently selected from the amino acid side chains of a proteinogenic or a non-proteinogenic alpha-amino acid having, the N-terminus thereof being the N—$R^7$, or may form a cyclic side chain with $R^7$;

stereocentres 1*, 2* and 3* are each independently selected from R and S;

wherein Z is an amino terminus of an amino acid; —C═O— adjacent L is the carboxy terminus of an amino acid; and Z along with L and —C═O— is a proteogenic or non-proteogenic amino acid or peptide or peptidomimetic; and n is 1, 2, 3, or 4 and where n is 2-4, each $R^8$ and each $R^9$ are independent of each other.

In an aspect, there is provided a compound of formula (III),

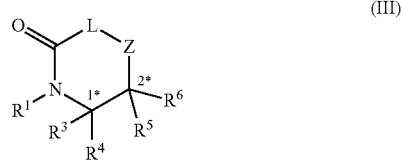

(III)

wherein $R^1$, $R^3$, $R^4$, $R^5$ and $R^6$ are each independently selected from the group consisting of H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH$_2$C(O)R, wherein R is selected from —OH, lower alkyl, aryl, -loweralkyl-aryl, or —NRaRb, where Ra and Rb are independently selected from H, lower alkyl, aryl or -loweralkyl-aryl; —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;

provided that $R^3$ or $R^4$ can be covalently linked to $R^1$ to form a cyclic secondary amine, and/or to $R^5$ or $R^6$ to form a ring; $R^3$ and $R^4$ may be covalently bound to each other to form a ring; and $R^5$ and $R^6$ may be covalently bound to each other to form a ring;

stereocentres 1* and 2* and 3* are independently selected from R and S; and

Z-L-C═O is an amino acid.

The following examples are illustrative of various aspects of the invention, and do not limit the broad aspects of the invention as disclosed herein.

Examples

Preparation of Fragments—Generic Synthetic Scheme

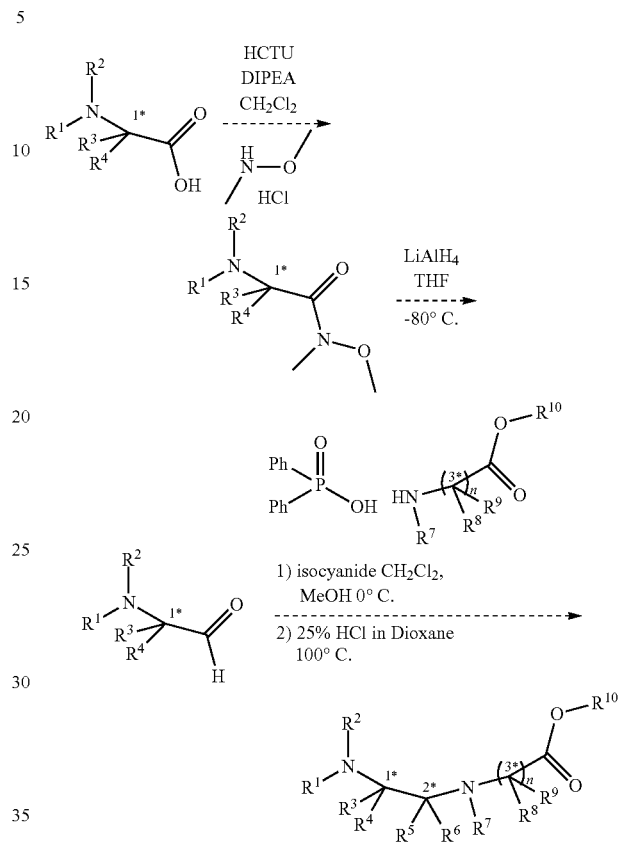

For instances where $R^3$, $R^4$, $R^5$ and $R^6$═H $R^5$ and $R^6$═H but one of $R^3$ or $R^4$≠H, a further scheme was employed.

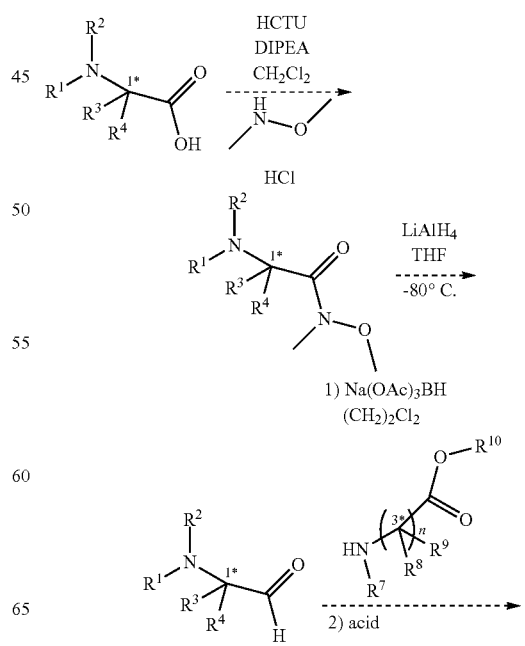

-continued

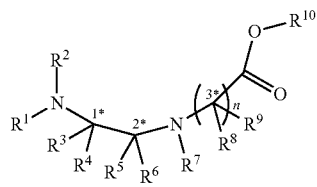

Preparation of Fragments

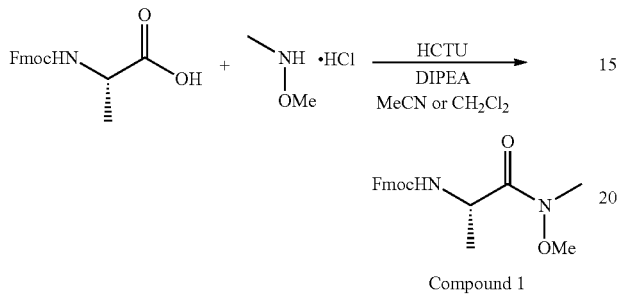

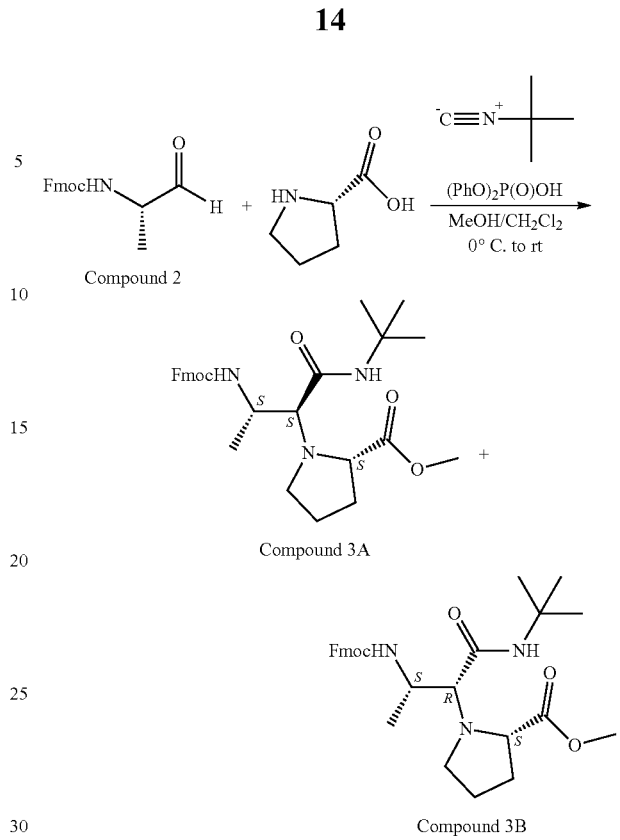

Reaction Molarity: 0.15 M

A mixture of Fmoc-L-Ala-OH (9.6 g, 30.7 mmol), N,O-dimethylhydroxylamine.HCl (3.6 g, 36.8 mmol), and HCTU (15.24 g, 36.8 mmol) in $CH_2Cl_2$ (200 mL), was cooled to 0° C. DIPEA (16.04 mL, 92.1 mmol) was then slowly added to the stirring mixture. The cooling bath was removed and the reaction was stirred at room temperature (rt) for 16 h. A 10% solution of HCl (100 mL) was added resulting in the formation of a precipitate, which was removed through filtration. The filtrate was washed with 10% HCl (3×100 mL) and brine (2×100 mL). The organic phase was then dried over $Na_2SO_4$. The solvent was removed under reduced pressure to give crude Compound 1 (10.5 g, 29.6 mmol, 97% yield), which was used in the next reaction without purification.

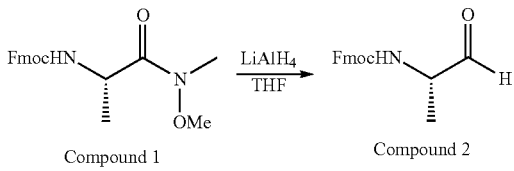

Reaction Molarity: 0.12 M

Lithium aluminum hydride powder (3.5 g, 92.1 mmol) was placed in a dry, 1 L flask. THF (Sigma-Aldrich, 250 ppm of BHT, ACS reagent >99.0%, 200 mL) was added, and the resulting slurry was cooled to −78° C., with stirring. To the slurry was added a solution of the crude Compound 1 (30 g; effective quantity estimated to be 21.7 g, 61.4 mmol) in THF (300 mL). The reaction vessel was transferred to an ice/water bath, and maintained at 0° C. for 1 h. To the reaction at 0° C., was added dropwise acetone (50 mL), then $H_2O$ (5 mL) and then the reaction was left to stir for an additional hour at rt. The mixture was filtered through Celite, washed with EtOAc (300 mL) and MeOH (300 mL), and the filtrate was concentrated. The crude material was dissolved in $CHCl_3$ (200 mL) and washed with brine (2×100 mL) and the organic phase was then dried over $Na_2SO_4$, filtered and concentrated to give Compound 2 as a white solid, 13.0 g (44 mmol, 72% yield for two steps).

Reaction Molarity: 0.055 M

Ugi reaction: to a solution of Compound 2 (13.0 g, 44.0 mmol) in MeOH (400 mL) and $CH_2Cl_2$ (200 mL) was added tert-butyl isocyanide (5 mL, 44.0 mmol) and diphenyl phosphate (1.1 g, 4.4 mmol). The reaction was then cooled to 0° C. and a solution of H-L-Pro-OH (5.06 g, 44.0 mmol) in MeOH (200 mL) was added dropwise over 5 h. The temperature was then warmed up to rt and the reaction was left to stir overnight. LC-MS analysis showed that the reaction was complete, and a mixture of diastereomers had formed. The solvent was evaporated, and the crude material was filtered over silica gel using a solution of 50% EtOAc/Hexane as an eluent. The solution was concentrated to give a mixture of Compound 3A, having S,S,S-stereochemistry across stereocentres 1*, 2* and 3* [see Formula (I) and Formula (II)] and Compound 3B, having S,R,S-stereochemistry across stereocentres 1*, 2* and 3* [see Formula (I) and Formula (II)]. The mixture was a white-yellow solid (17.2 g, 78%).

A further consideration to the synthesis of Compounds 3A and 3B, and related analogs, is the practical outcome in terms of the balance between the desired chemical entities and potential side-products. For example, when the Ugi reaction is conducted at 0° C. in DCM and MeOH solvents with no Bronsted or Lewis acid, the following HPLC traces of the crude reaction mixture were obtained (FIG. 1a, FIG. 1b).

Figures 2A, 2B:
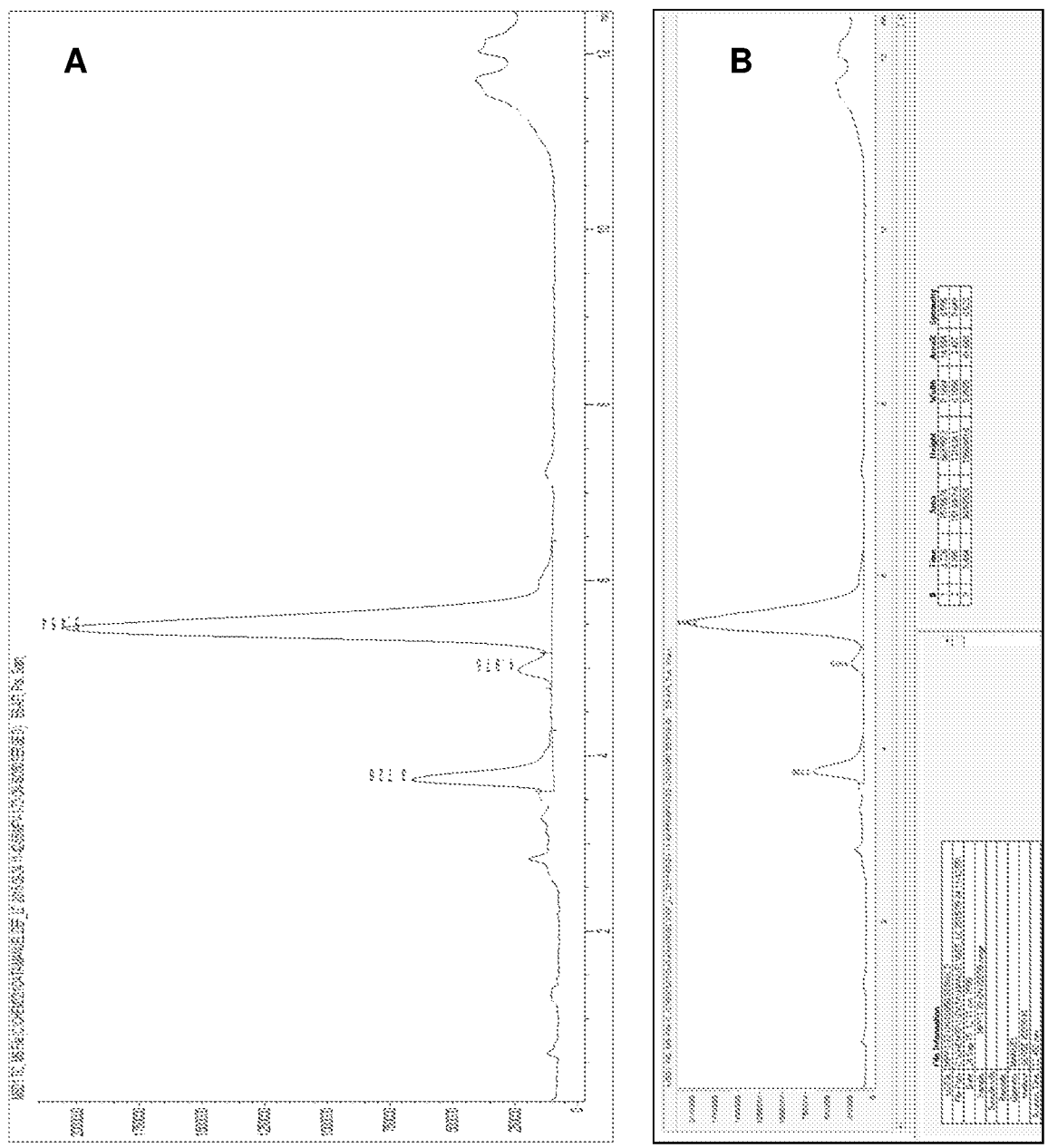
FIG. 2a is a LC trace of a Ugi reaction conducted at 10° C. in dichloromethane and methanol in the presence of 10 mol % of an acid such as diphenyl phosphate
FIG. 2b is a LC trace of a Ugi reaction conducted at 10° C. in dichloromethane and methanol in the presence of 10 mol % of an acid such as diphenyl phosphate.

In contrast, when 10 mol % of an acid such as diphenyl phosphate is added to the reaction in these solvents at 0° C., the following LC traces were obtained (FIG. 2a, FIG. 2b).

The acid-mediated Ugi reaction produces a cleaner crude profile trace than the Ugi reaction conducted in the absence of an acid.

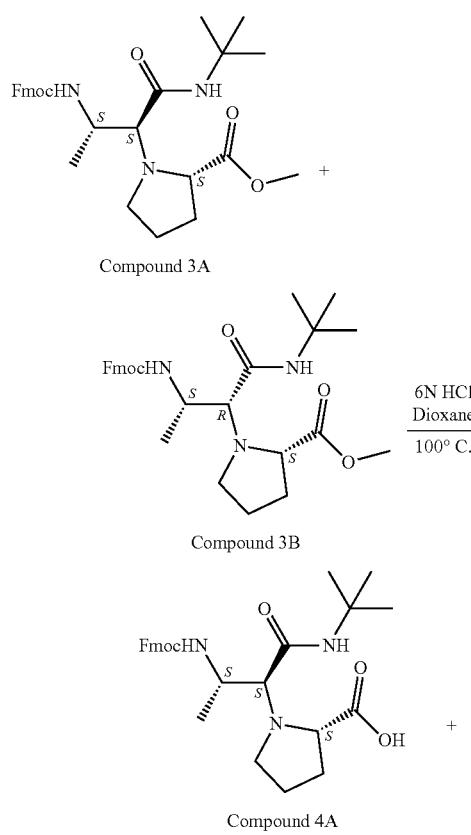

Compound 3A

Compound 3B

Compound 4A

Compound 4B

Reaction Molarity: 0.295 M

To the crude mixture of Compound 3A and Compound 3B (17.2 g, 34 mmol) in dioxane (300 mL) was added 25% HCl (16 mL) at ambient temperature. The mixture was stirred at 100° C. for 36 h. LC-MS analysis showed that the reaction was complete. The solvent was concentrated under reduced pressure and the solid-oil was dissolved in $CH_2Cl_2$ (20 mL) and diluted with a solution of 50% EtOAc/Hexane (200 mL), the formed solid was filtered over Celite and then washed with MeOH. The MeOH was evaporated and the solid residue (14.8 g, 88% yield of crude) was purified via reverse-phase silica chromatography. CombiFlash conditions of 28%-40% MeCN (containing 0.1% formic acid) in water (containing 0.1% formic acid) were employed to separate the diastereomers and afforded Compound 4A, a fragment with S,S,S-stereochemistry (9.45 g, 56% yield) and Compound 4B, a fragment with S,R,S-stereochemistry (1.0 g, 6% yield. The 50% EtOAc/Hexane filtrate was also later concentrated under reduced pressure to reveal an additional 3.75 g of a crude mixture of Compounds 4A and 4B.

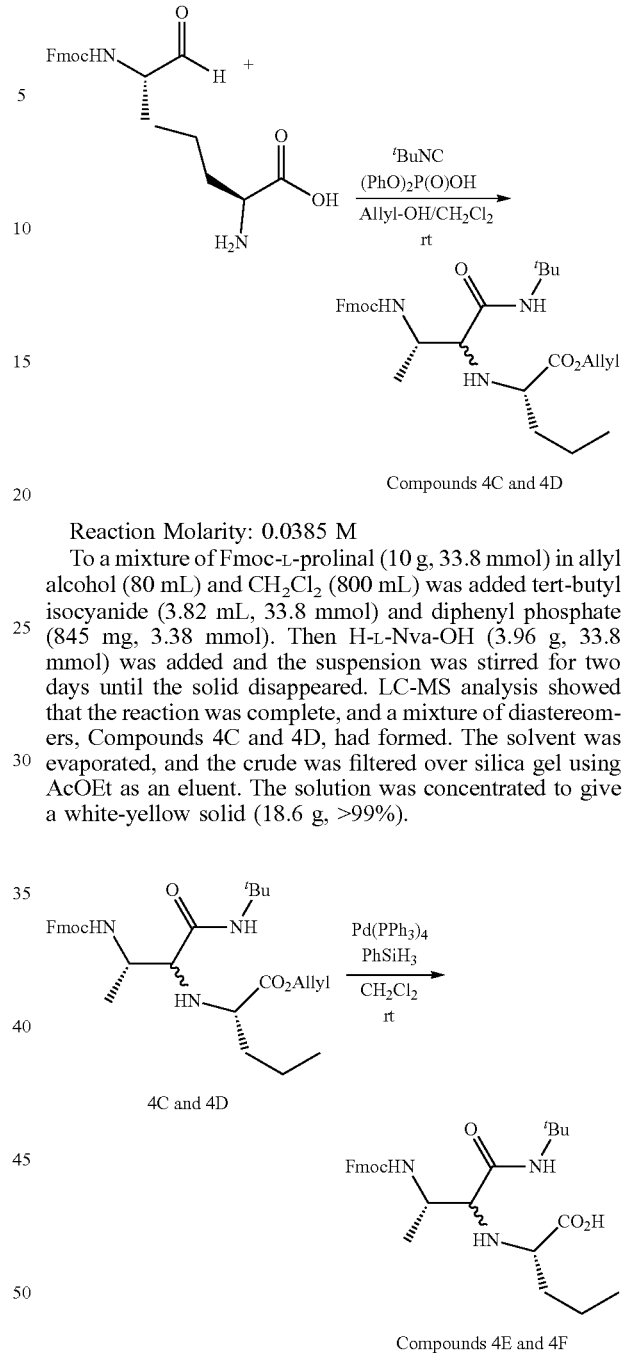

Compounds 4C and 4D 4C and 4D

Compounds 4E and 4F

Reaction Molarity: 0.0385 M

To a mixture of Fmoc-L-prolinal (10 g, 33.8 mmol) in allyl alcohol (80 mL) and $CH_2Cl_2$ (800 mL) was added tert-butyl isocyanide (3.82 mL, 33.8 mmol) and diphenyl phosphate (845 mg, 3.38 mmol). Then H-L-Nva-OH (3.96 g, 33.8 mmol) was added and the suspension was stirred for two days until the solid disappeared. LC-MS analysis showed that the reaction was complete, and a mixture of diastereomers, Compounds 4C and 4D, had formed. The solvent was evaporated, and the crude was filtered over silica gel using AcOEt as an eluent. The solution was concentrated to give a white-yellow solid (18.6 g, >99%).

To the crude 4C and 4D diastereomer mixture (3.22 g, 6.0 mmol) in dry $CH_2Cl_2$ (75 mL) and under $N_2$ atmosphere, was added $Pd(PPh_3)_4$ (347 mg, 0.3 mmol) and $PhSiH_3$ (2.21 mL, 18.0 mmol). After 30 minutes, the reaction turned red/brown in color. LC-MS analysis showed that the reaction was complete after 1 h. MeOH (100 mL) was added to the flask and the mixture was stirred for an additional 30 minutes. The solvent was evaporated, and the crude material was filtered over charcoal using AcOEt as an eluent. The solvent was removed and the crude material was purified via reverse-phase silica chromatography. CombiFlash purification conditions: 36-40% MeCN (containing 0.1% formic acid) in water (containing 0.1% formic acid). The fractions were concentrated giving diastereomer 4E (780 mg, 26%) and diastereomer 4F (350 mg, 12%).

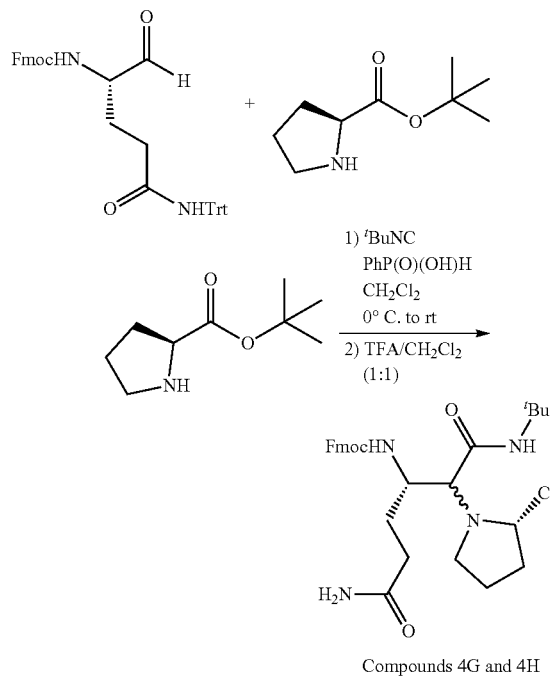

Compounds 4G and 4H

Reaction Molarity: 0.046 M

To a mixture of Fmoc-L-Gln(Trt)-H (34.25 g, 57.61 mmol; prepared via LiAlH$_4$-mediated reduction of the corresponding Weinreb amide derivative of Fmoc-L-Gln(Trt)-OH, analogous to the two-step transformation of Fmoc-L-Ala-OH to Compounds 1 and 2) in CH$_2$Cl$_2$ (1250 mL) was added tert-butyl isocyanide (6.49 mL, 57.61 mmol) and phenylphosphinic acid (2.0 g, 14.32 mmol). Then H-L-Pro-O$^t$Bu (9.05 mL, 57.61 mmol) was added and the reaction was stirred overnight. LC-MS analysis (after treatment with TFA) showed that the reaction was complete. The solvent was evaporated, the crude material was diluted with a solution of TFA/CH$_2$Cl$_2$ (1:1, 200 mL), and the mixture was stirred for 24 h. LC-MS analysis showed that the reaction was complete, and a mixture of diastereomers had formed. The solvent was removed and the crude material was purified via reverse-phase silica chromatography. CombiFlash purification conditions: 25-35% MeCN (containing 0.1% formic acid) in water (containing 0.1% formic acid). The fractions were concentrated giving diastereomer 4G (4.1 g, 9.5%) and diastereomer 4H (5.9 g, 13.5%).

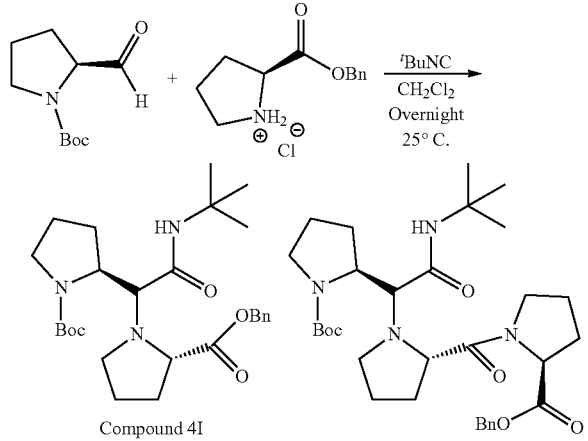

Compound 4I

Reaction Molarity: 0.25 M

To a mixture of Boc-L-prolinal (100 mg, 0.5 mmol) and H-L-Pro-OBn.HCl (121 mg, 0.5 mmol) in CH$_2$Cl$_2$ (2 mL) was added tert-butyl isocyanide (0.057 mL, 0.5 mmol) and the reaction was stirred overnight. LC-MS analysis showed that the reaction was complete (ratio 83:17, desired product: side product). The solvent was removed and the crude material was purified via reverse-phase silica chromatography. CombiFlash purification conditions: 40-55% MeCN (containing 0.1% formic acid) in water (containing 0.1% formic acid). The solution was concentrated to give Compound 41 as a white solid (86.1 mg, 35%).

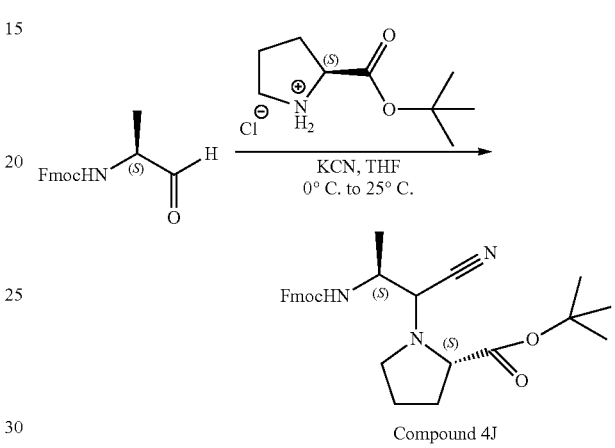

Compound 4J

To a solution of Fmoc-L-prolinal (5.0 g, 16.95 mmol) in a mixture of THF (250 mL) and H$_2$O (10 mL) at 0° C. were added KCN (1.1 g, 16.95 mmol) and H-L-Pro-O$^t$Bu.HCl (3.5, 16.95 mmol). The reaction was stirred overnight at room temperature and monitored by LC-MS. Then, the solvent was evaporated and the crude material was dissolved in AcOEt (250 mL). The organic phase was washed with brine (3×100 mL), dried over Na$_2$SO$_4$, filtered and evaporated. The crude was then dissolved in CH$_2$Cl$_2$ and filtered over silica gel. The solution was concentrated to give Compound 4J a white-yellow oil (5.5 g, 60%).

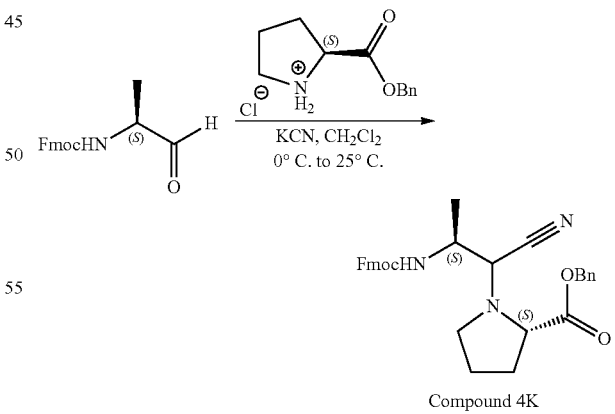

Compound 4K

To a solution of Fmoc-L-prolinal (5.0 g, 16.95 mmol) in a mixture of CH$_2$Cl$_2$ (250 mL) and H$_2$O (10 mL) at 0° C. were added KCN (1.1 g, 16.95 mmol) and H-L-Pro-OBn.HCl (4.09, 16.95 mmol). The reaction was stirred overnight at room temperature and monitored by LC-MS. Then, the solvent was quenched with HCl (10%, 100 mL) and the mixture was extracted with CH$_2$Cl$_2$ (3×100 mL).

The organic phase was dried over Na$_2$SO$_4$, filtered and evaporated. The solution was concentrated to give Compound 4K a white-yellow oil (6.5 g, 70%).

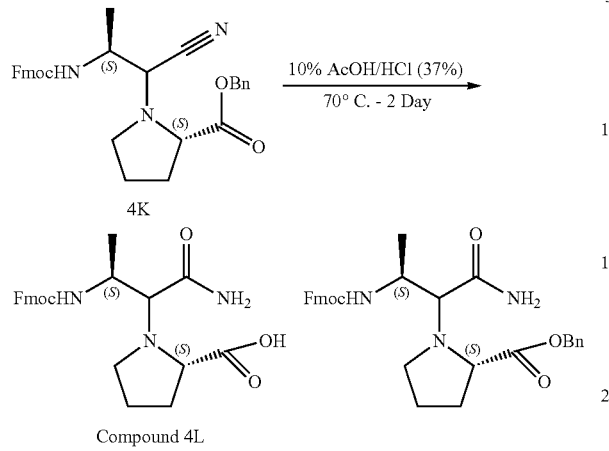

Compound 4L

A suspension of the nitrile 4K (1.0 g, 1.96 mmol) in a 10% solution of AcOH in HCl conc. (15 mL) and H$_2$O (10 mL) was placed in a sealed tube and refluxed at 70° C. for 2 days. The reaction was monitored by LC-MS. Then, the solid was filtered and washed with CH$_2$Cl$_2$. The solvent was removed and the crude material was purified via reverse-phase silica chromatography. CombiFlash purification conditions: 35-55% MeCN (containing 0.1% formic acid) in water (containing 0.1% formic acid). The solution was concentrated to give Compound 4L as a white solid (368 mg, 43%).

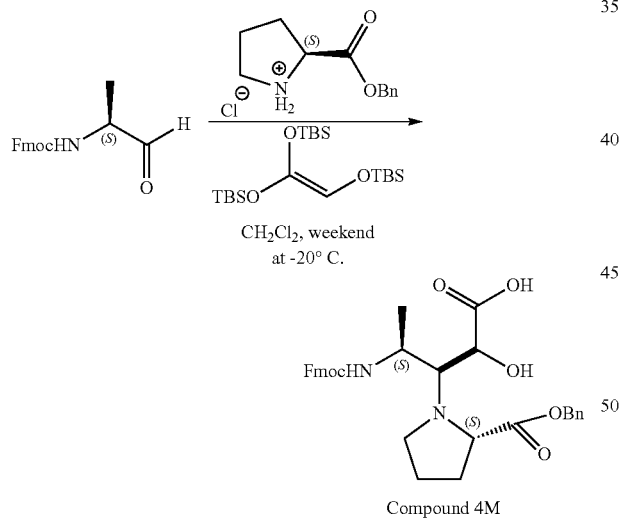

Compound 4M

To a solution of Fmoc-l-alaninal (3.3 g, 11.1 mmol; Compound 2) in dry CH$_2$Cl$_2$ (50 mL) under inert atmosphere at 0° C. were added H-L-Pro-OBn.HCl (2.7 g, 11.1 mmol) and tris(trimethylsiloxy)ethylene (4.3 mL, 13.3 mmol). The reaction was placed in the fridge over the weekend at −20° C. and monitored by LC-MS. The solvent was removed and the crude material was purified via reverse-phase silica chromatography. CombiFlash purification conditions: 35-55% MeCN (containing 0.1% formic acid) in water (containing 0.1% formic acid). The solution was concentrated to give Compound 4M as a white solid (3.3 g, 52%).

Alternatively, the initial use of a tert-butoxycarbonyl group to protect the amino terminus (N-Boc) of an amino acid provides complementary access to preparative quantities of fragments, as documented below.

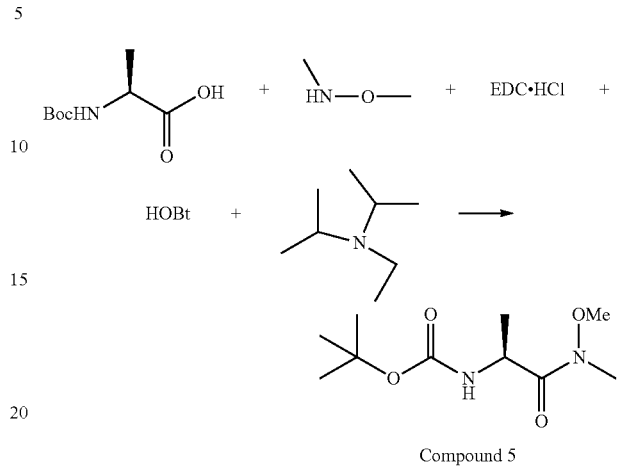

Compound 5

Reaction Molarity: 0.255 molar

To the mixture of Boc-L-Ala-OH (5.8 g, 30.7 mmol), N,O-dimethylhydroxylamine.HCl (3.59 g, 36.8 mmol), EDC.HCl (7.05 g, 36.8 mmol), 1H-benzo[d][1,2,3]triazol-1-ol.H$_2$O (5.63 g, 36.8 mmol) in DCM (120 mL), was slowly added DIPEA (8.54 mL, 49.0 mmol) under stirring. The reaction mixture was left at rt for 16 h, then diluted with 360 mL EtOAc. The solution was washed with 0.2 N HCl (2×100 mL), sat. NaHCO$_3$ (2×100 mL) and brine (2×100 mL), then dried over MgSO$_4$. The solvent was removed under reduced pressure to give Compound 5 (6.85 g, 29.5 mmol, 96% yield), which was pure enough for the next step without purification.

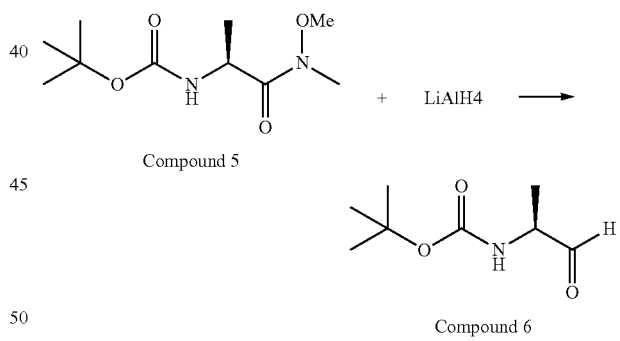

Compound 6

Reaction Molarity: 0.210 M

Compound 5 (6.84 g, 29.4 mmol) was dissolved in THF (140 mL), cooled to −78° C., and 1 M LiAlH$_4$ in THF (32.4 mL, 32.4 mmol) was added dropwise. After 2 h, the temperature was raised from −78° C. to −30° C., and the reaction was quenched with 0.5 N HCl (80 mL) and EtOAc (400 mL). Phases were separated, and the organic phase was washed again with 0.1 N HCl (80 mL), sat. NaHCO$_3$ (80 mL), brine (80 mL), and dried over MgSO$_4$. NMR showed about 20% amide was not reduced. The crude oil was purified by flash chromatography and eluted with 20-40% EtOAc in Hexanes to give Compound 6 (3.2 g, 18.47 mmol, 62.7% yield) as a white solid (Rf=0.58; 40% EtOAc in Hex); and then 60-100% EtOAc was used to elute the starting Weinreb amide (1.78 g was recovered, Rf=0.33).

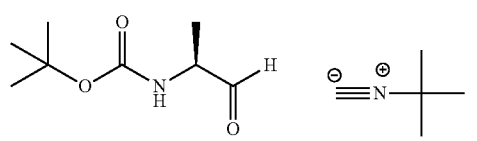

Compound 6

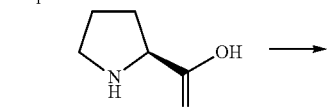

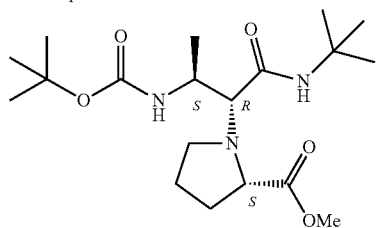

Compound 7A

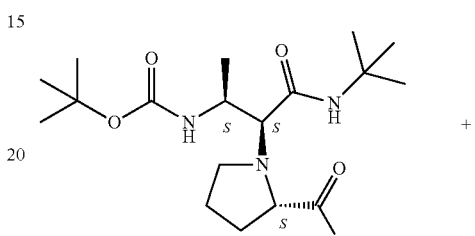

Compound 7B

Reaction Molarity: 0.090 molar

To a mixture of Compound 6 (3.11 g, 17.96 mmol) and H-L-Pro-OH (2.171 g, 18.85 mmol) in MeOH (200 mL) was added tert-butyl isocyanide (2.028 mL, 17.96 mmol) at rt. The reaction mixture was stirred at rt for 42 h. LC-MS analysis showed that the reaction was complete. Direct flash silica gel purification gave two diastereoisomers, Compound 7A, with S,S,S-stereochemistry (3.7 g, 9.60 mmol, 53.5% yield; Rf=0.41, 40% EtOAc in Hex) and Compound 7B, with S,R,S-stereochemistry (0.7 g, 1.816 mmol, 10.11% yield; Rf=0.46, 40% EtOAc in Hex).

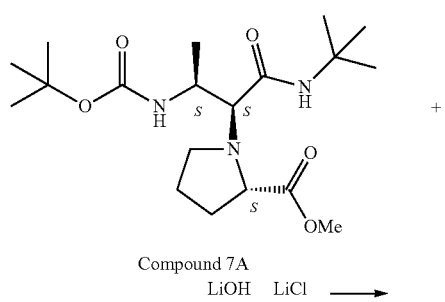

Compound 7A
LiOH   LiCl  ⟶

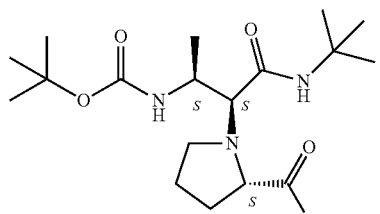

Compound 8

Reaction Molarity: 0.156 M

To Compound 7A (3.6 g, 9.34 mmol) in THF (60 mL) and 1 M lithium chloride (14.01 mL, 14.01 mmol) was added 1 M lithium hydroxide (14.01 mL, 14.01 mmol) at 0° C. The reaction mixture was stirred at 0° C. to room temperature for 4 h. LC-MS analysis showed that the reaction was complete. The solution was acidified to pH 2 with 1 N HCl, and extracted with EtOAc (4×100 mL). The combined organic phase was washed with brine (100 mL) and dried over MgSO₄. The solvent was removed under reduced pressure to give Compound 8 with S,S,S-stereochemistry (3.5 g, 9.42 mmol, 101% yield), which was used in the next reaction without purification.

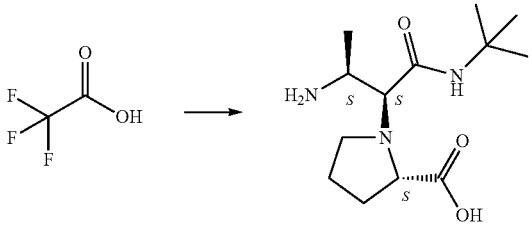

Compound 8

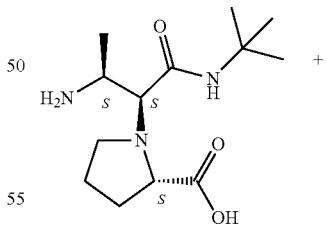

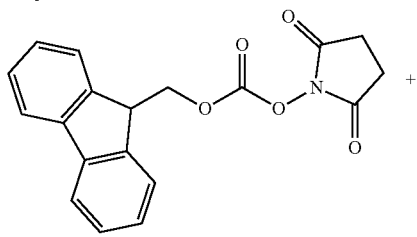

Compound 9

Reaction Molarity: 0.174 molar

To Compound 8 (3.5 g, 9.42 mmol) in DCM (54 mL) was added 2,2,2-trifluoroacetic acid (10.82 mL, 141 mmol) at 0° C. The reaction mixture was stirred at 0° C. to room temperature for 2 h. LC-MS analysis showed that the reaction was complete. The solvent was removed under reduced pressure to give crude Compound 9 with S,S,S-stereochemistry (2.7 g, 9.95 mmol, 106% yield), which was used in the next reaction without purification.

Compound 9

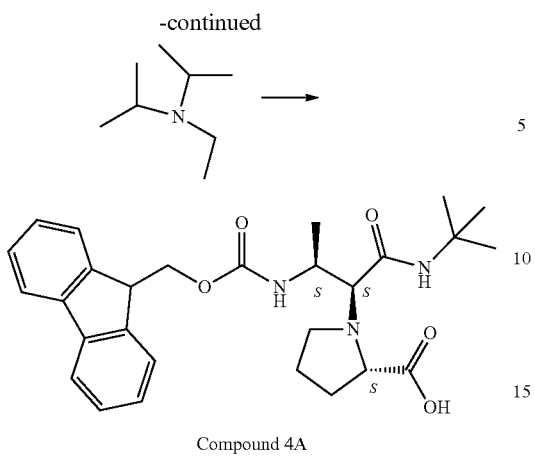

Compound 4A

Reaction Molarity: 0.142 molar

To a mixture of Compound 9 (2.7 g, 9.95 mmol) and Fmoc-OSu (3.69 g, 10.95 mmol) in DCM (70 mL) was added DIPEA (3.64 mL, 20.90 mmol) at 0° C. The reaction mixture was stirred at 0° C. to room temperature for 2 h. LC-MS analysis showed that the reaction was complete. The mixture was diluted with EtOAc (300 mL), washed with 0.2 N HCl (2×80 mL) and brine (80 mL), dried and evaporated. Flash silica gel purification (20% EtOAc in Hex to 100% EtOAc, then 15% MeOH in EtOAc with 0.05% HOAc) gave Fmoc-protected Compound 4A (2.4 g, 4.86 mmol, 48.9% yield; Rf=0.25, 10% MeOH in DCM).

Note that a fully-deprotected fragment can be cyclized head-to-tail as part of a strategy to prepare piperazinones and facilitate determination of the stereochemical outcome of the Ugi reaction. The additional constraints in the resulting cyclic structure lend themselves to full structure determination by 2D NMR techniques. For example, Compound 7A when treated with an acid to remove the N-Boc protecting group, can then be treated with a base to mediate cyclization by direct amidation from the free amine to the C-terminus methyl ester:

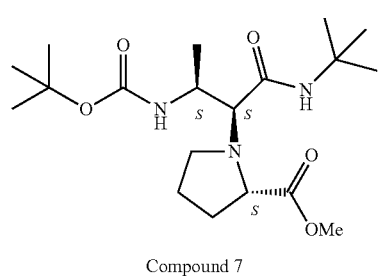

Compound 7

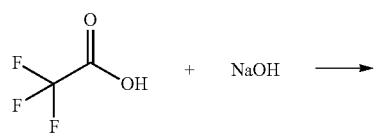

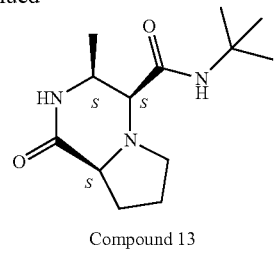

Compound 13

To a mixture of Compound 7 (120 mg, 0.311 mmol) in DCM (3 ml) was added 2,2,2-trifluoroacetic acid (0.596 ml, 7.78 mmol) at 0° C. The reaction mixture was stirred from 0° C. to rt for 2 h. LC-MS showed reaction is complete. The reaction mixture was concentrated to dryness and the residue was dissolved in DCM (5 ml), cooled to 0° C. 1 N sodium hydroxide (1.556 mL, 1.556 mmol) was added to pH 10. The mixture was stirred for 1 h and then extracted with DCM (3×10 mL). The combined DCM was dried over MgSO₄ and concentrated. The crude was purified by flash silica gel purification (20-100% AcOEt, then 10% MeOH in AcOEt) to give Compound 13 (55 mg, 0.217 mmol, 69.7% yield) Rf=0.45 (10% MeOH in DCM).

Preparation of Macrocycles from Fragments—Generic Synthetic Scheme

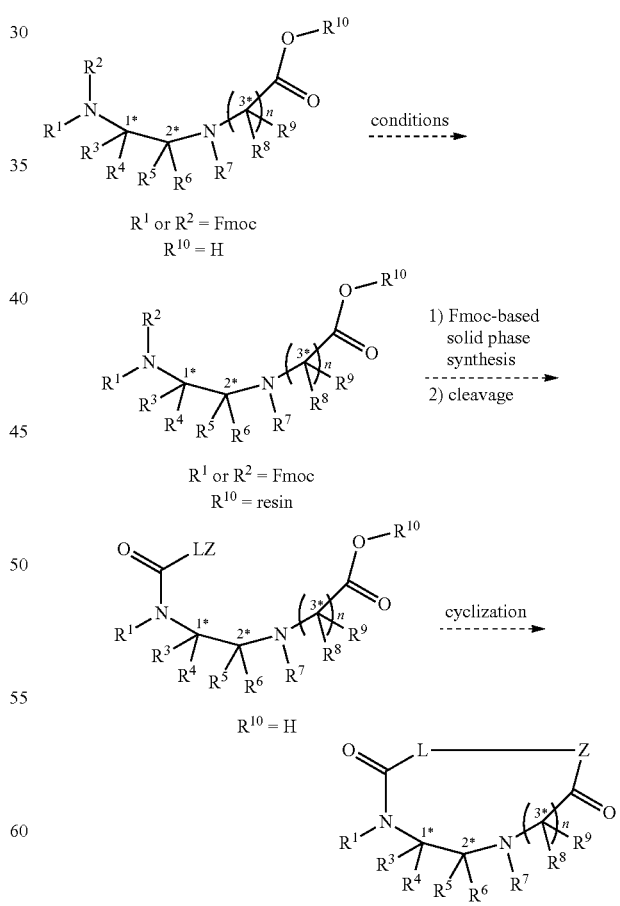

The above generic scheme depicts head-to-tail cyclization from an amino terminus of an amino acid (Z) onto the C-terminus carboxylic acid of the fragment.

Preparation of Macrocycles from Fragments—Synthetic Scheme

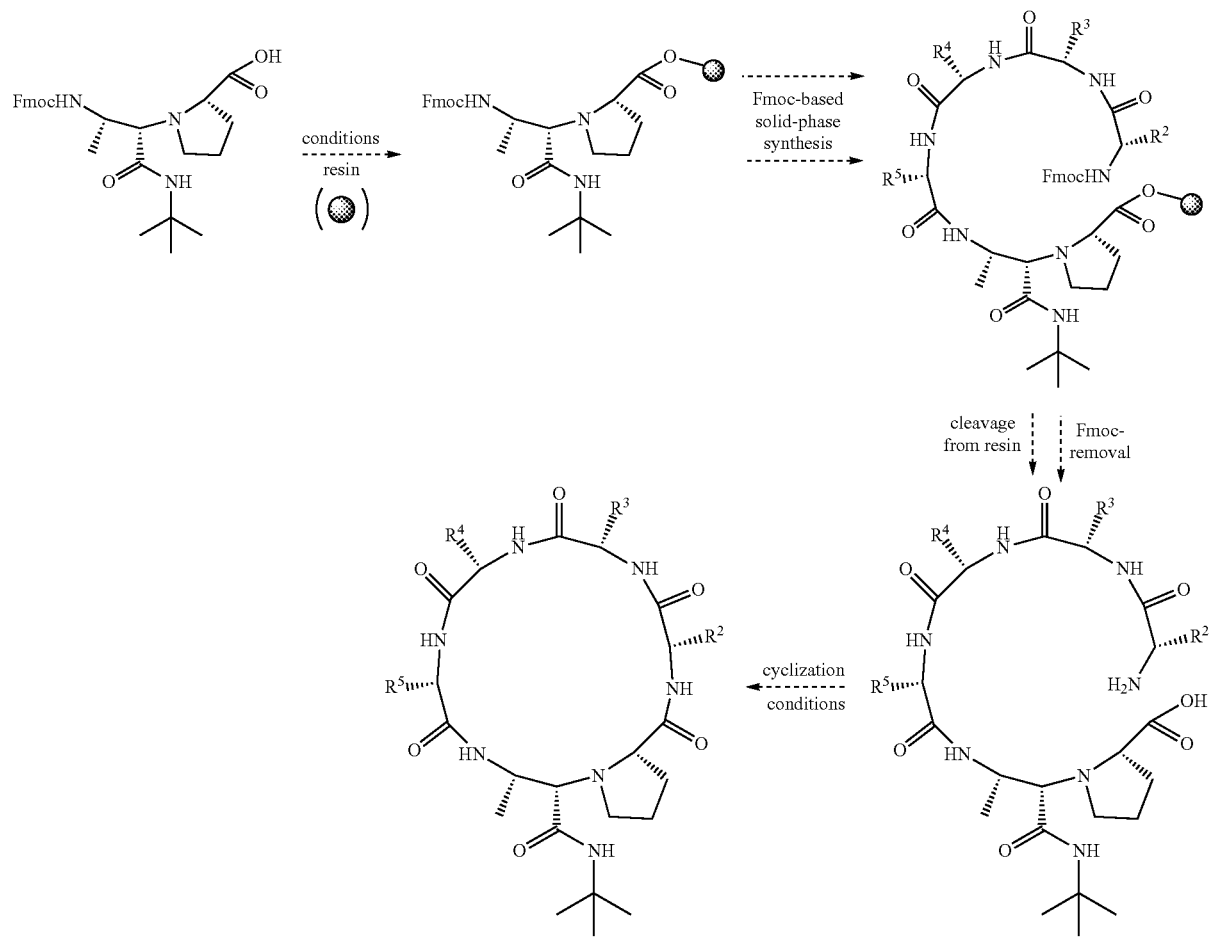

Preparation of Macrocycles from Fragment—General Experimental Protocol

Fmoc-Fragment Amino Acid Loading onto 2-Cl Trt Resin

An Fmoc-protected fragment such as Compound 4A (1.1 eq. respective to resin) was dissolved in DCM (10 mL/g of resin). The 2-chlorotrityl resin was allowed to swell in DCM (5 mL/g of resin) for 15 minutes. The DCM was then drained and the Fmoc-fragment amino acid solution was added to the vessel containing the 2-Cl Trt resin. 2 eq. (respective to the amino acid) of DIPEA was added and the vessel was agitated for 5 minutes. Another 2 eq. of DIPEA was then added and the vessel was left to agitate for an additional 90 minutes. The resin was then treated with methanol (1 mL/g of resin) to endcap any remaining reactive 2-Cl Trt groups. The solution was mixed for 15 minutes, drained and then rinsed with DCM (×3), DMF (×3), DCM (×2) and MeOH (×3). The resin was then dried under vacuum and weighed to determine the loading of the Fmoc-protected fragment onto the resin.

Peptide Synthesis

Fully protected resin-bound peptides were synthesized via standard Fmoc solid-phase peptide chemistry manually or using an automated peptide synthesizer. All N-Fmoc amino acids were employed. Fmoc removal was achieved by treatment with 20% piperidine in NMP twice, for 5 and 10 minutes respectively, with consecutive DMF and NMP washes after each addition. For all Fmoc amino acid couplings, the resin was treated with 3 eq. of Fmoc amino acid, 3 eq. of HATU and 6 eq. of DIPEA in NMP or DMF for 60 minutes. For difficult couplings, a second treatment with 3 eq. of Fmoc amino acid, 3 eq. of HATU and 6 eq. of DIPEA in NMP for 40 minutes was employed. Once the peptide was synthesized, following Fmoc removal, the resin was treated with 1:3, HFIP:DCM, twice for 30 minutes each, to afford cleavage from the solid support. The solvent was then removed, followed by trituration with tert-butyl methyl ether to give the linear peptide. The purity was then analyzed by reversed-phase HPLC-MS.

Cyclization

In a two-dram vial, 0.1 mmol of the linear peptide and DEPBT (1.5 eq.) were dissolved in 5 mL of freshly distilled THF (0.02 M). DIPEA (3 eq.) was then added and the reaction mixture was left to stir overnight at room temperature (16 h). Tetraalkylammonium carbonate resin (6 eq.) was then added to the reaction mixture and stirring was continued for an additional 24 h. The reaction was then filtered through a solid phase extraction vessel and rinsed with DCM (2 mL). Alternatively, after macrocyclization, a 7 M solution of ammonia in methanol (Sigma-Aldrich; 10 eq.) was added and stirring was continued for an additional 24 h. The reaction was then filtered through a solid phase extraction vessel and rinsed with DCM. The filtrate and washes were combined and the solvent was removed under reduced pressure. Deprotection of the side chain protecting groups was achieved by dissolving the peptides in 2 mL of a cleavage cocktail consisting of TFA:H$_2$O:triisopropylsilane (95:2.5:2.5) for two hours. Subsequently, the cleavage mixture was evaporated under reduced pressure and the peptides were precipitated twice from diethyl ether/hexanes. Peptide macrocycles were then purified by reversed-phase Flash chromatography and lyophilized.

Supporting Data

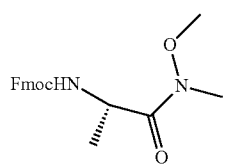

Compound 1:
$^1$H NMR (500 MHz, Chloroform-d) δ 7.76 (ddt, J=7.6, 1.2, 0.7 Hz, 2H), 7.64-7.58 (m, 2H), 7.39 (ttd, J=7.5, 1.1, 0.6 Hz, 2H), 7.31 (tdd, J=7.4, 2.1, 1.2 Hz, 2H), 5.67 (d, J=8.4 Hz, 1H), 4.76 (t, J=7.4 Hz, 1H), 4.43-4.30 (m, 2H), 4.22 (t, J=7.3 Hz, 1H), 3.77 (s, 3H), 3.22 (s, 3H), 1.37 (d, J=6.8 Hz, 3H); MW: 354.41 g/mol; LC-MS m/z: 355.2

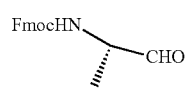

Compound 2:
$^1$H NMR (500 MHz, Chloroform-d) δ 9.56 (s, 1H), 7.77 (d, J=7.5 Hz, 2H), 7.60 (d, J=8.0 Hz, 2H), 7.45-7.39 (m, 2H), 7.33-7.29 (m, 2H), 5.41 (d, J=4.2 Hz, 1H), 4.50-4.39 (m, 2H), 4.32 (p, J=7.2 Hz, 1H), 4.23 (t, J=6.8 Hz, 1H), 1.38 (d, J=7.3 Hz, 3H); MW: 295.3 g/mol

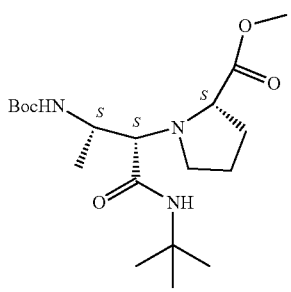

Compound 7A:
$^1$H NMR (400 MHz, Chloroform-d) δ 6.43 (s, 1H), 5.59 (br s, 1H), 4.05-3.90 (m, 1H), 3.83 (dd, J=9.0, 2.7 Hz, 1H), 3.67 (s, 3H), 3.18 (d, J=4.3 Hz, 1H), 3.00-2.92 (m, 2H), 2.23-2.03 (m, 1H), 1.91-1.77 (m, 3H), 1.41 (s, 9H), 1.32 (s, 9H), 1.22 (d, J=6.8 Hz, 3H); MW: 385.5 g/mol; LC-MS m/z: 386.3

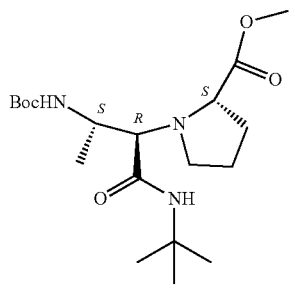

Compound 7B:
$^1$H NMR (400 MHz, Chloroform-d) δ 7.13 (s, 1H), 5.53 (d, J=9.2 Hz, 1H), 4.07-3.90 (m, 1H), 3.69 (s, 3H), 3.60-3.52 (m, 1H), 3.14 (d, J=4.0 Hz, 1H), 3.01 (ddd, J=9.3, 6.3, 3.7 Hz, 1H), 2.81 (td, J=8.8, 6.5 Hz, 1H), 2.07 (dtd, J=12.6, 10.2, 9.8, 7.7 Hz, 1H), 1.93-1.75 (m, 3H), 1.40 (s, 9H), 1.31 (s, 9H), 1.15 (d, J=6.6 Hz, 3H); MW: 385.5 g/mol; LC-MS m/z: 386.3

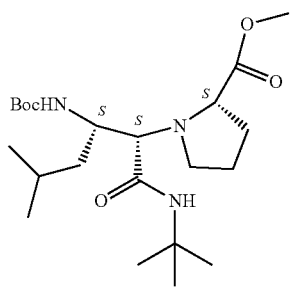

Compound 10:
MW: 427.58 g/mol; LC-MS m/z: 428.3

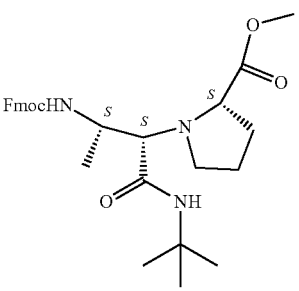

Compound 3A:
MW: 507.6 g/mol; LC-MS m/z: 508.2

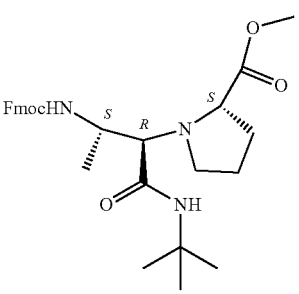

Compound 3B:
MW: 507.6 g/mol; LC-MS m/z: 508.2

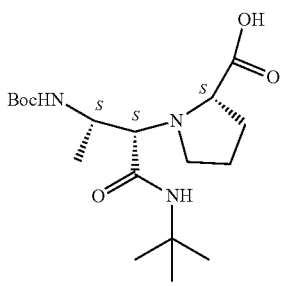

Compound 8:
MW: 371.5 g/mol; LC-MS m/z: 372.3

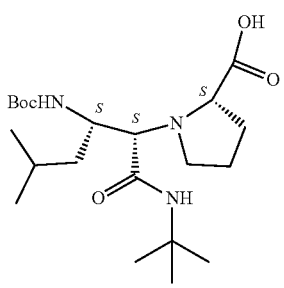

Compound 11:
MW: 413.55 g/mol; LC-MS m/z: 414.3

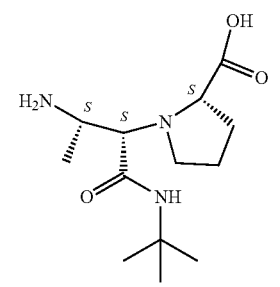

Compound 9:
MW: 271.4 g/mol; LC-MS m/z: 272.3

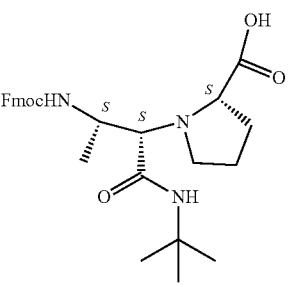

Compound 4A:
$^1$H NMR (700 MHz, DMSO-d$_6$) δ 12.23 (s, 1H), 7.88 (dt, J=7.6, 0.8 Hz, 2H), 7.68-7.63 (m, 2H), 7.41 (ddt, J=8.5, 7.5, 0.8 Hz, 2H), 7.33-7.28 (m, 2H), 7.20 (s, 1H), 6.85 (d, J=8.6 Hz, 1H), 4.30-4.23 (m, 2H), 4.19 (t, J=6.9 Hz, 1H), 3.81 (ddt, J=15.2, 8.5, 6.4 Hz, 1H), 3.44 (dd, J=8.8, 5.1 Hz, 1H), 3.24 (d, J=8.6 Hz, 1H), 3.20-3.15 (m, 1H), 2.86 (td, J=7.9, 4.0 Hz, 1H), 1.95 (dq, J=12.4, 8.3 Hz, 1H), 1.77 (ddt, J=12.7, 8.2, 4.9 Hz, 1H), 1.72-1.61 (m, 2H), 1.20 (s, 9H), 1.11 (d, J=6.6 Hz, 3H). $^{13}$C NMR (126 MHz, DMSO-d$_6$) δ 175.54, 170.30, 155.51, 144.28, 141.13, 128.00, 127.99, 127.43, 127.42, 125.50, 120.51, 66.12, 65.74, 62.84, 50.77, 47.40, 47.20, 47.13, 29.69, 28.72, 23.87, 19.36; MW: 493.6 g/mol; LC-MS m/z: 494.2

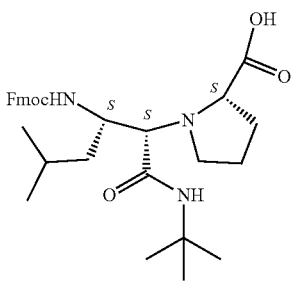

Compound 12:
MW: 535.67 g/mol; LC-MS m/z: 536.3

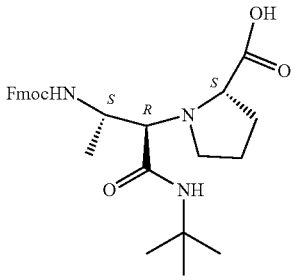

Compound 4B:
$^1$H NMR (700 MHz, DMSO-d$_6$) δ 12.14 (s, 1H), 7.88 (dt, J=7.5, 0.9 Hz, 2H), 7.70 (s, 1H), 7.65 (d, J=7.5 Hz, 2H), 7.43-7.39 (m, 2H), 7.32 (td, J=7.4, 1.1 Hz, 2H), 6.85 (d, J=8.2 Hz, 1H), 4.33 (dd, J=10.4, 6.9 Hz, 1H), 4.28-4.18 (m, 2H), 3.87-3.78 (m, 2H), 3.25 (d, J=6.3 Hz, 1H), 2.93 (td, J=8.0, 3.7 Hz, 1H), 2.72 (q, J=7.8 Hz, 1H), 2.00-1.92 (m, 1H), 1.79 (ddt, J=12.5, 7.5, 2.7 Hz, 1H), 1.75-1.65 (m, 2H), 1.24 (s, 9H), 1.06 (d, J=6.6 Hz, 3H). $^{13}$C NMR (126 MHz, DMSO-d$_6$) δ 176.60, 170.97, 155.51, 144.34, 144.30, 141.20, 141.18, 128.07, 127.51, 125.57, 125.50, 120.60, 120.58, 120.50, 66.61, 65.77, 60.96, 50.82, 50.79, 47.38, 47.22, 30.36, 28.74, 23.95, 19.10; MW: 493.6 g/mol; LC-MS m/z: 494.2

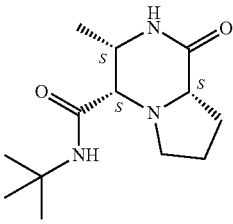

Compound 13:
$^1$H NMR (400 MHz, Benzene-d$_6$) δ 6.50 (s, 1H), 6.03 (s, 1H), 3.27 (pd, J=6.9, 1.9 Hz, 1H), 2.90-2.77 (m, 2H), 2.68 (t, J=8.3 Hz, 1H), 2.17 (dddd, J=12.9, 11.0, 9.0, 6.9 Hz, 1H), 1.91 (q, J=8.7 Hz, 1H), 1.83-1.72 (m, 1H), 1.50 (ddtd,

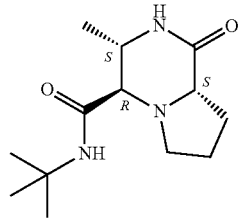

Compound 14:

¹H NMR (400 MHz, Benzene-d₆) δ 7.98 (s, 1H), 6.78 (s, 1H), 3.46 (t, J=7.7 Hz, 1H), 3.22 (dqd, J=9.2, 6.5, 1.6 Hz, 1H), 2.72-2.64 (m, 2H), 2.31-2.16 (m, 2H), 1.91 (dtd, J=12.3, 8.2, 3.8 Hz, 1H), 1.49-1.39 (m, 1H), 1.37 (d, J=6.5 Hz, 3H), 1.34-1.27 (m, 1H), 1.25 (s, 9H); MW: 253.4 g/mol; LC-MS m/z: 254.3

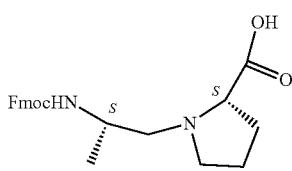

Compound 15:

¹H NMR (500 MHz, DMSO-d₆) δ 7.88 (dt, J=7.7, 1.0 Hz, 2H), 7.69 (dd, J=8.0, 2.9 Hz, 2H), 7.44-7.38 (m, 2H), 7.33 (tt, J=7.4, 1.3 Hz, 2H), 7.26 (d, J=8.1 Hz, 1H), 4.27 (dtd, J=40.9, 13.7, 12.1, 7.2 Hz, 3H), 3.66 (p, J=6.9 Hz, 1H), 3.33 (dd, J=14.1, 5.5 Hz, 1H), 3.25-3.19 (m, 1H), 2.78 (dd, J=12.3, 7.4 Hz, 1H), 2.64 (dd, J=12.2, 6.5 Hz, 1H), 2.57 (q, J=8.4 Hz, 1H), 2.03 (dq, J=12.7, 8.5 Hz, 1H), 1.87-1.65 (m, 3H), 1.08 (d, J=6.5 Hz, 3H); MW: 394.5 g/mol; LC-MS m/z: 395.2

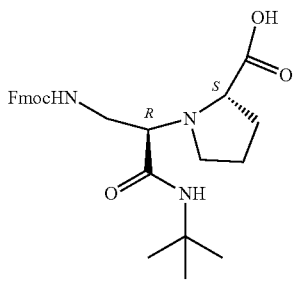

Compound 16:

¹H NMR (500 MHz, DMSO-d₆) δ 8.21 (s, 1H), 7.91-7.86 (m, 2H), 7.71-7.66 (m, 2H), 7.41 (tt, J=7.5, 1.5 Hz, 2H), 7.32 (ddt, J=7.4, 5.9, 1.2 Hz, 2H), 7.17 (t, J=5.7 Hz, 1H), 4.32-4.18 (m, 3H), 3.75-3.69 (m, 1H), 3.42 (dd, J=8.6, 5.4 Hz, 1H), 3.38-3.31 (m, 1H), 3.24 (dt, J=15.2, 7.8 Hz, 1H), 2.79-2.69 (m, 1H), 1.98-1.89 (m, 1H), 1.77 (td, J=8.4, 7.9, 3.5 Hz, 1H), 1.72-1.56 (m, 3H), 1.24 (d, J=4.1 Hz, 9H); MW: 479.6 g/mol; LC-MS m/z: 480.2

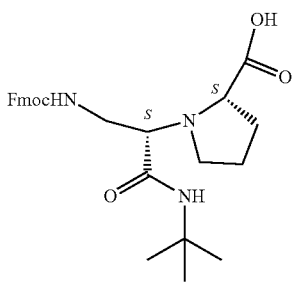

Compound 17:

¹H NMR (500 MHz, DMSO-d₆) δ 7.89 (ddt, J=7.5, 1.2, 0.6 Hz, 2H), 7.72 (s, 1H), 7.71-7.66 (m, 2H), 7.41 (tdd, J=6.9, 1.2, 0.6 Hz, 2H), 7.36-7.29 (m, 3H), 4.31-4.17 (m, 3H), 3.55 (dd, J=9.4, 4.1 Hz, 1H), 3.41 (t, J=7.1 Hz, 1H), 3.29-3.18 (m, 1H), 3.01 (t, J=8.7 Hz, 1H), 2.90 (q, J=8.3 Hz, 1H), 2.03-1.91 (m, 1H), 1.83 (tt, J=7.6, 3.8 Hz, 1H), 1.75-1.55 (m, 2H), 1.24 (s, 9H); MW: 479.6 g/mol; LC-MS m/z: 480.2

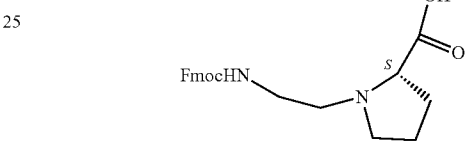

Compound 18:

¹H NMR (500 MHz, Chloroform-d) δ 7.89 (dt, J=7.5, 0.9 Hz, 2H), 7.68 (d, J=7.5 Hz, 2H), 7.41 (tdt, J=7.4, 1.1, 0.5 Hz, 2H), 7.33 (ddt, J=8.4, 7.4, 1.1 Hz, 3H), 4.33 (d, J=6.7 Hz, 2H), 4.26-4.19 (m, 1H), 3.40 (dd, J=9.2, 5.0 Hz, 1H), 3.37-3.31 (m, 1H), 3.22-3.18 (m, 2H), 2.96 (dt, J=13.5, 6.9 Hz, 1H), 2.79 (dt, J=12.3, 6.1 Hz, 1H), 2.68 (q, J=9.2 Hz, 1H), 2.09 (dq, J=12.9, 8.8 Hz, 1H), 1.85 (dtd, J=23.0, 8.2, 7.8, 4.2 Hz, 2H), 1.68 (dt, J=12.6, 8.3 Hz, 1H).

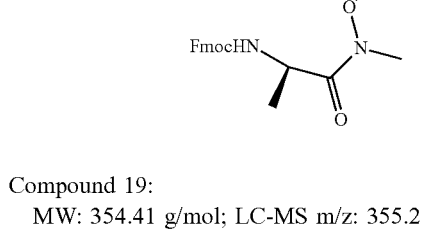

Compound 19:
MW: 354.41 g/mol; LC-MS m/z: 355.2

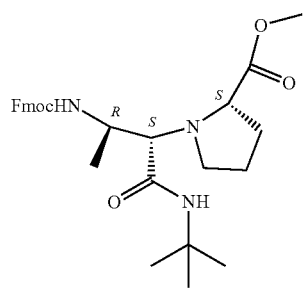

Compound 20:
MW: 507.6 g/mol; LC-MS m/z: 508.2

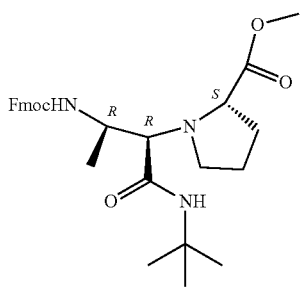

Compound 21:
MW: 507.6 g/mol; LC-MS m/z: 508.2

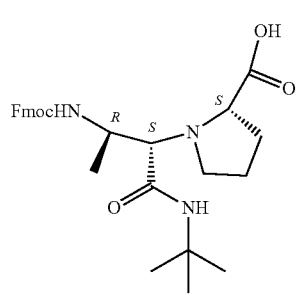

Compound 22:
MW: 493.6 g/mol; LC-MS m/z: 494.2

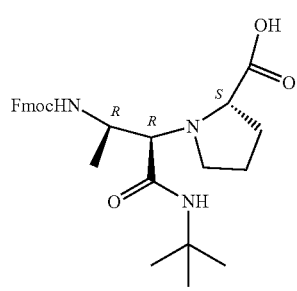

Compound 23:
¹H NMR (400 MHz, DMSO-d₆) δ 7.87 (d, J=7.5 Hz, 2H), 7.68 (s, 1H), 7.63 (d, J=7.5 Hz, 2H), 7.43-7.36 (m, 2H), 7.30 (td, J=7.5, 1.1 Hz, 2H), 6.84 (d, J=8.2 Hz, 1H), 4.35-4.16 (m, 3H), 3.81 (td, J=10.8, 9.9, 4.7 Hz, 2H), 3.22 (d, J=6.3 Hz, 1H), 2.90 (d, J=9.3 Hz, 1H), 2.70 (q, J=7.7 Hz, 1H), 2.01-1.87 (m, 1H), 1.84-1.62 (m, 3H), 1.22 (s, 9H), 1.04 (d, J=6.6 Hz, 3H); MW: 493.6 g/mol; LC-MS m/z: 494.2

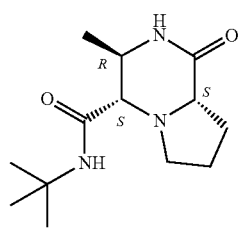

Compound 24:
¹H NMR (400 MHz, Benzene-d₆) δ 6.79 (s, 1H), 6.23 (s, 1H), 3.68-3.55 (m, 1H), 3.54-3.46 (m, 1H), 3.10-3.04 (m, 1H), 2.75 (ddd, J=9.4, 6.5, 2.7 Hz, 1H), 2.24 (ddt, J=13.1, 10.5, 7.7 Hz, 1H), 2.04-1.88 (m, 2H), 1.39-1.27 (m, 2H), 1.26 (s, 9H), 0.97 (ddd, J=8.7, 5.3, 2.7 Hz, 3H).

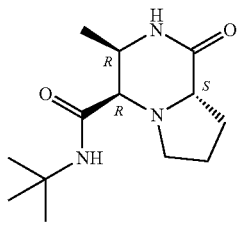

Compound 25:
¹H NMR (400 MHz, Benzene-d₆) δ 7.85 (s, 1H), 6.12 (s, 1H), 3.97-3.79 (m, 1H), 3.19-3.08 (m, 1H), 2.82 (d, J=9.7 Hz, 1H), 2.70 (td, J=8.5, 6.0 Hz, 1H), 2.31 (td, J=8.6, 5.8 Hz, 1H), 2.17 (ddt, J=12.8, 10.0, 6.4 Hz, 1H), 1.97 (dddd, J=13.0, 9.9, 8.3, 4.9 Hz, 1H), 1.48 (dddd, J=10.0, 7.5, 6.2, 3.8 Hz, 1H), 1.42-1.33 (m, 1H), 1.30 (d, J=6.3 Hz, 3H), 1.22 (s, 9H).

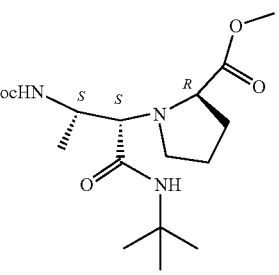

Compound 26:
MW: 507.6 g/mol; LC-MS m/z: 508.2

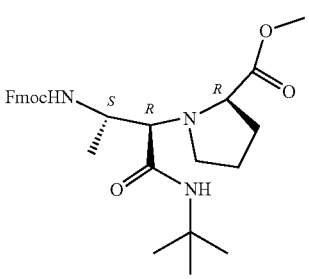

Compound 27:
MW: 507.6 g/mol; LC-MS m/z: 508.2

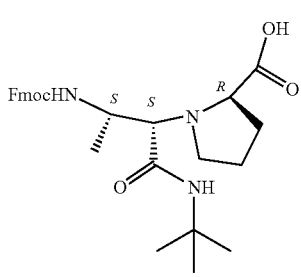

Compound 28:
MW: 493.6 g/mol; LC-MS m/z: 494.2

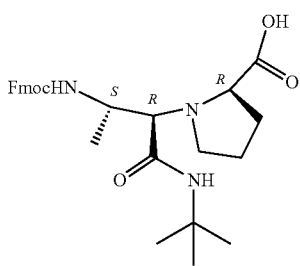

Compound 29:
MW: 493.6 g/mol; LC-MS m/z: 494.2

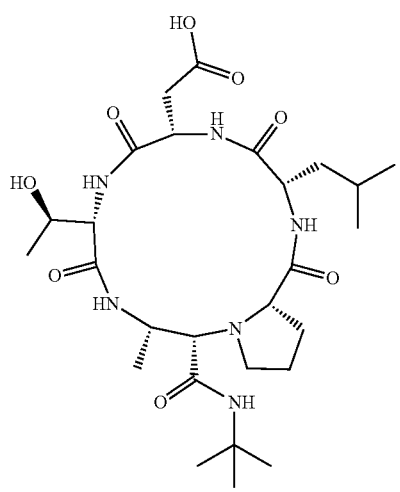 [SMILES: CC(C)C[C@@H]1NC(=O)[C@@H]2CCCN2[C@H](C(=O)NC(C)(C)C)[C@H](C)NC(=O)[C@H]([C@@H](C)O)NC(=O)[C@H](CC(=O)O)NC1=O]

Compound 30:
¹H NMR (500 MHz, DMSO-d₆) δ 8.69 (br s, 1H), 8.44-8.21 (m, 2H), 7.69 (br s, 1H), 7.61 (s, 1H), 4.38 (q, J=6.6 Hz, 1H), 4.33-4.24 (m, 1H), 4.12 (dd, J=10.0, 6.1 Hz, 1H), 4.08-3.99 (m, 1H), 3.92 (p, J=6.4 Hz, 1H), 3.62 (dd, J=17.0, 5.6 Hz, 1H), 3.20-3.12 (m, 1H), 3.06-2.95 (m, 1H), 2.54 (q, J=1.9 Hz, 0H), 2.46 (p, J=1.9 Hz, 1H), 1.99 (dq, J=11.8, 8.4 Hz, 1H), 1.81 (d, J=5.6 Hz, 1H), 1.75-1.56 (m, 2H), 1.48 (td, J=13.8, 12.5, 6.5 Hz, 2H), 1.23 (s, 9H), 1.15 (d, J=7.0 Hz, 3H), 1.01 (d, J=6.3 Hz, 3H), 0.89 (dd, J=14.2, 6.2 Hz, 6H); MW: 582.7 g/mol; LC-MS m/z: 583.4

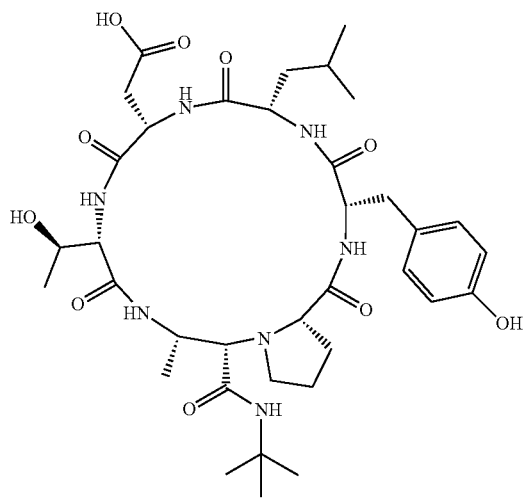 [SMILES: CC(C)C[C@@H]1NC(=O)[C@H](Cc2ccc(O)cc2)NC(=O)[C@@H]2CCCN2[C@H](C(=O)NC(C)(C)C)[C@H](C)NC(=O)[C@H]([C@@H](C)O)NC(=O)[C@H](CC(=O)O)NC1=O]

Compound 31:
¹H NMR (700 MHz, DMSO-d₆) δ 8.86 (br s, 2H), 7.65-7.50 (m, 2H), 7.04 (d, J=8.7 Hz, 1H), 6.99 (dd, J=8.6, 6.9 Hz, 2H), 6.95 (d, J=9.1 Hz, 1H), 6.74 (s, 1H), 6.66-6.62 (m, 2H), 4.53-4.46 (m, 1H), 4.31-4.24 (m, 2H), 4.20 (dq, J=8.7, 4.5 Hz, 1H), 4.10-4.02 (m, 1H), 4.00 (dd, J=9.1, 1.6 Hz, 1H), 3.31-3.21 (m, 2H), 3.09-3.02 (m, 1H), 3.01-2.91 (m, 2H), 2.88 (dt, J=9.1, 4.7 Hz, 1H), 2.80 (dt, J=16.2, 8.1 Hz, 1H), 2.77-2.69 (m, 1H), 1.90-1.83 (m, 1H), 1.74-1.54 (m, 6H), 1.45-1.35 (m, 1H), 1.19 (s, 9H), 1.07 (d, J=6.6 Hz, 3H), 1.00 (dd, J=6.6, 3.2 Hz, 3H), 0.96-0.89 (m, 3H), 0.87 (d, J=6.3 Hz, 3H); MW: 745.9 g/mol; LC-MS m/z: 746.4

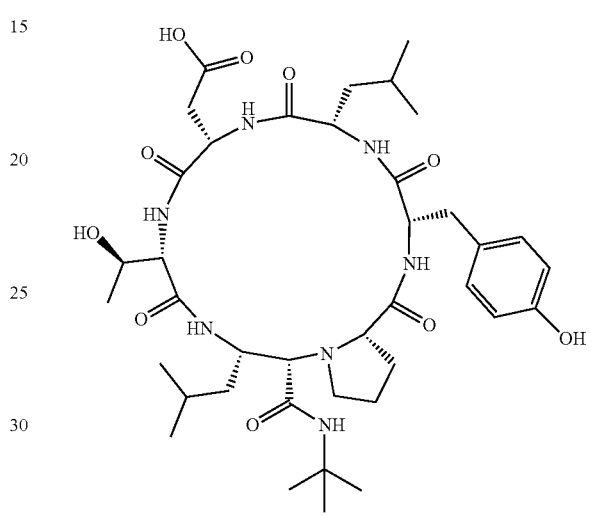

Compound 32:
MW: 787.9 g/mol; LC-MS m/z: 788.5

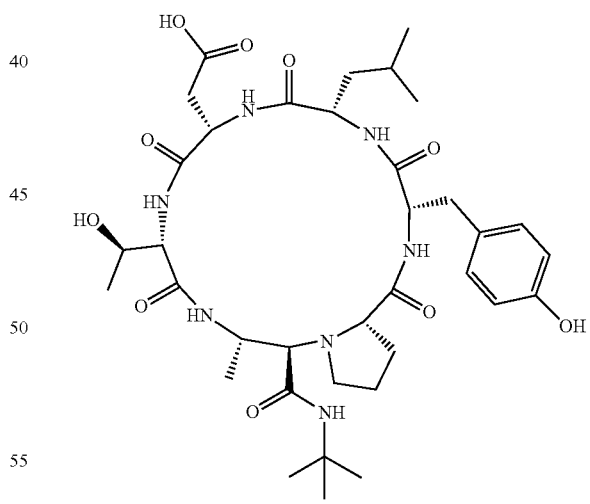

Compound 33:
¹H NMR (700 MHz, DMSO-d₆) δ 8.83 (br s, 1H), 8.70 (d, J=7.5 Hz, 1H), 8.43 (d, J=6.3 Hz, 1H), 7.88 (s, 1H), 7.68 (d, J=10.2 Hz, 1H), 7.40 (d, J=10.0 Hz, 1H), 7.05 (d, J=8.5 Hz, 2H), 6.63 (d, J=8.5 Hz, 2H), 4.65 (td, J=11.1, 10.5, 3.8 Hz, 1H), 4.35 (td, J=8.1, 4.3 Hz, 1H), 4.17 (dd, J=10.1, 3.4 Hz, 1H), 4.14-4.10 (m, 1H), 4.08-4.03 (m, 1H), 3.99 (d, J=10.3 Hz, 1H), 3.86 (td, J=7.6, 2.7 Hz, 1H), 3.30-3.24 (m, 1H), 3.00-2.94 (m, 2H), 2.88-2.76 (m, 3H), 2.73-2.65 (m, 1H), 1.71-1.63 (m, 1H), 1.58 (dt, J=14.5, 7.5 Hz, 1H), 1.49 (ddd, J=14.4, 8.5, 4.4 Hz, 2H), 1.46-1.39 (m, 1H), 1.23 (s, 9H), 1.20 (d, J=6.9 Hz, 3H), 1.09 (dd, J=11.2, 5.2 Hz, 1H), 1.05 (d, J=6.4 Hz, 3H), 0.93 (d, J=6.5 Hz, 3H), 0.88 (d, J=6.6 Hz, 3H), 0.86-0.79 (m, 1H); MW: 745.9 g/mol; LC-MS m/z: 746.6

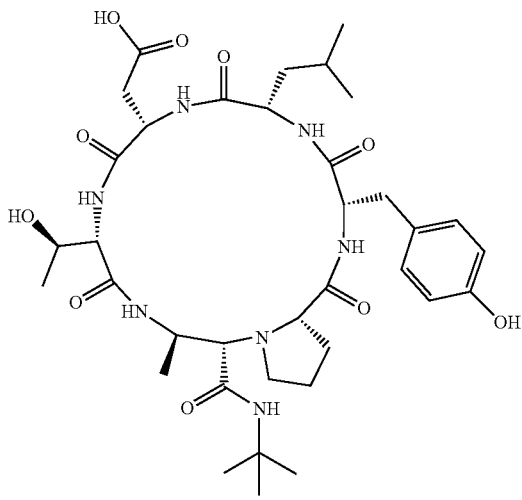 [SMILES: CC(C)C[C@@H]1NC(=O)[C@H](Cc2ccc(O)cc2)NC(=O)[C@@H]2CCCN2[C@H](C(=O)NC(C)(C)C)[C@@H](C)NC(=O)[C@H]([C@@H](C)O)NC(=O)[C@H](CC(=O)O)NC1=O]

Compound 34:
$^1$H NMR (700 MHz, DMSO-d$_6$) δ 9.00 (br s, 1H), 7.58 (d, J=9.7 Hz, 1H), 7.53 (s, 1H), 7.05-6.96 (m, 3H), 6.94 (d, J=8.9 Hz, 1H), 6.73 (s, 1H), 6.68-6.58 (m, 2H), 4.49 (dt, J=9.7, 7.3 Hz, 1H), 4.29 (tt, J=7.0, 3.4 Hz, 1H), 4.26-4.18 (m, 2H), 4.10-4.02 (m, 1H), 3.98 (dd, J=9.0, 1.6 Hz, 1H), 3.28-3.21 (m, 2H), 3.06 (dd, J=8.6, 7.3 Hz, 1H), 2.96 (d, J=7.3 Hz, 2H), 2.91-2.85 (m, 1H), 2.78-2.70 (m, 1H), 2.66 (dd, J=17.1, 3.9 Hz, 1H), 1.87 (dq, J=12.3, 8.1 Hz, 1H), 1.72-1.61 (m, 3H), 1.62-1.54 (m, 2H), 1.41 (dddd, J=12.5, 8.6, 7.0, 5.5 Hz, 1H), 1.20 (s, 9H), 1.06 (d, J=6.5 Hz, 3H), 1.00 (d, J=6.4 Hz, 3H), 0.92 (d, J=6.3 Hz, 3H), 0.86 (d, J=6.4 Hz, 3H). $^{13}$C NMR (126 MHz, DMSO-d$_6$) δ 174.3, 173.4, 172.2, 171.8, 171.1, 169.8, 169.0, 156.4, 130.5, 127.9, 115.3, 65.9, 65.9, 64.4, 57.8, 54.4, 53.3, 51.8, 50.9, 46.5, 45.8, 41.4, 36.5, 35.8, 29.6, 28.5, 24.6, 23.8, 23.7, 21.4, 21.0, 19.2; MW: 745.9 g/mol; LC-MS m/z: 746.4

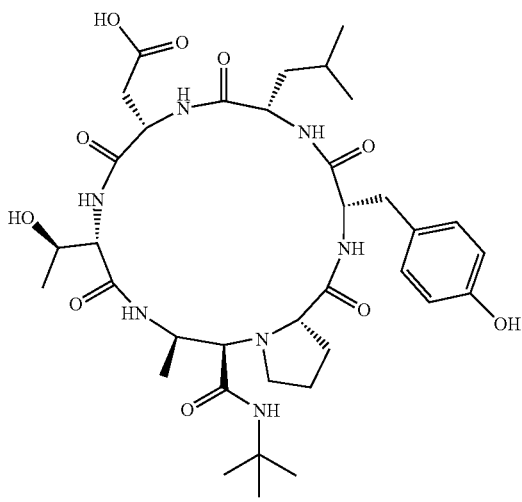 [SMILES: CC(C)C[C@@H]1NC(=O)[C@H](Cc2ccc(O)cc2)NC(=O)[C@@H]2CCCN2[C@@H](C(=O)NC(C)(C)C)[C@@H](C)NC(=O)[C@H]([C@@H](C)O)NC(=O)[C@H](CC(=O)O)NC1=O]

Compound 35:
MW: 745.9 g/mol; LC-MS m/z: 746.5

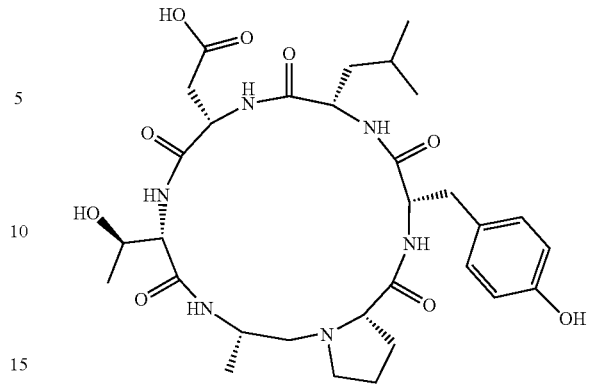

Compound 36:
Mixture of conformers, 1:1 ratio.
$^1$H NMR (500 MHz, DMSO-d$_6$) δ 8.94 (d, J=3.3 Hz, 1H), 8.71 (d, J=6.7 Hz, 1H), 8.52 (d, J=7.4 Hz, 1H), 8.29 (br s, 1H), 7.94 (d, J=6.9 Hz, 1H), 7.75 (d, J=10.4 Hz, 1H), 7.70 (d, J=9.7 Hz, 1H), 7.50 (d, J=10.0 Hz, 1H), 7.33-7.22 (m, 2H), 7.05-6.98 (m, 4H), 6.65-6.58 (m, 4H), 4.94 (br s, 1H), 4.85 (d, J=5.5 Hz, 1H), 4.63 (td, J=10.4, 5.0 Hz, 1H), 4.54 (td, J=10.3, 4.3 Hz, 1H), 4.37 (ddd, J=8.9, 7.2, 4.3 Hz, 1H), 4.30-4.23 (m, 2H), 4.16-4.08 (m, 2H), 4.09-4.01 (m, 2H), 3.97 (td, J=7.5, 4.2 Hz, 1H), 3.78 (tt, J=6.8, 3.2 Hz, 1H), 3.20-3.15 (m, 3H), 3.12-3.00 (m, 3H), 2.92-2.71 (m, 6H), 2.71-2.64 (m, 1H), 2.44 (t, J=11.9 Hz, 1H), 2.39-2.32 (m, 1H), 2.30-2.15 (m, 2H), 2.12-2.03 (m, 1H), 1.93-1.78 (m, 2H), 1.70-1.48 (m, 7H), 1.49-1.40 (m, 2H), 1.39-1.31 (m, 1H), 1.30-1.20 (m, 2H), 1.13 (d, J=6.8 Hz, 3H), 1.08-0.98 (m, 6H), 0.96 (d, J=6.6 Hz, 3H), 0.92-0.87 (m, 9H), 0.87-0.80 (m, 3H); MW: 646.7 g/mol; LC-MS m/z: 647.3

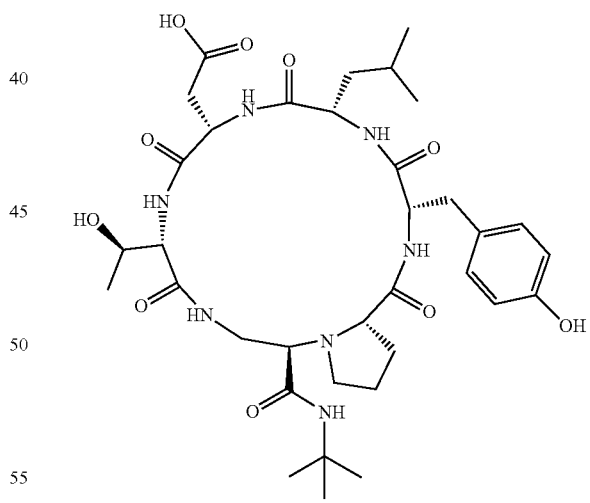

Compound 37:
$^1$H NMR (500 MHz, DMSO-d$_6$) δ 8.85 (br s, 1H), 8.78 (d, J=7.4 Hz, 1H), 8.55 (t, J=5.7 Hz, 1H), 7.74 (s, 1H), 7.64 (d, J=9.8 Hz, 1H), 7.59 (d, J=10.1 Hz, 1H), 7.06-7.00 (m, 2H), 6.67-6.62 (m, 2H), 4.80 (br s, 1H), 4.62-4.52 (m, 1H), 4.23 (ddd, J=10.2, 4.3, 2.4 Hz, 2H), 4.03 (dd, J=9.4, 1.6 Hz, 1H), 3.94-3.83 (m, 2H), 3.56 (dd, J=10.6, 2.8 Hz, 1H), 3.30-3.23 (m, 2H), 2.87 (dt, J=24.8, 8.4 Hz, 2H), 2.80-2.73 (m, 3H), 2.69-2.59 (m, 1H), 1.66 (dt, J=13.3, 6.6 Hz, 1H), 1.61-1.47 (m, 4H), 1.43 (t, J=5.9 Hz, 1H), 1.23 (s, 9H), 1.06 (d, J=6.3

Hz, 3H), 1.01 (t, J=3.2 Hz, 1H), 0.94 (d, J=6.5 Hz, 3H), 0.88 (d, J=6.5 Hz, 3H); MW: 731.8 g/mol; LC-MS m/z: 732.4

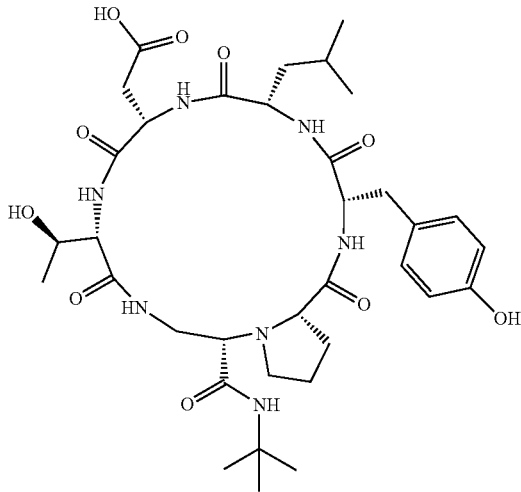 [SMILES: CC(C)C[C@@H]1NC(=O)[C@H](Cc2ccc(O)cc2)NC(=O)[C@@H]2CCCN2[C@H](C(=O)NC(C)(C)C)CNC(=O)[C@H]([C@@H](C)O)NC(=O)[C@H](CC(=O)O)NC1=O]

Compound 38:

$^1$H NMR (500 MHz, DMSO-d$_6$) δ 8.92 (br s, 1H), 8.76 (br s, 1H), 7.88 (d, J=10.5 Hz, 1H), 7.68 (d, J=7.7 Hz, 1H), 7.54 (s, 1H), 7.35 (d, J=9.9 Hz, 1H), 7.05 (d, J=8.5 Hz, 2H), 6.61 (d, J=8.5 Hz, 2H), 5.08 (br s, 1H), 4.60 (td, J=11.0, 4.1 Hz, 1H), 4.29 (q, J=6.3 Hz, 1H), 4.24 (dd, J=10.0, 3.1 Hz, 1H), 4.07-4.00 (m, 1H), 3.92 (dd, J=12.0, 8.5 Hz, 1H), 3.87 (ddd, J=9.0, 5.9, 3.1 Hz, 1H), 3.41-3.36 (m, 1H), 3.19-3.08 (m, 2H), 3.05 (dd, J=9.8, 4.3 Hz, 1H), 2.96 (d, J=13.2 Hz, 1H), 2.92-2.82 (m, 2H), 2.70-2.61 (m, 1H), 2.50-2.42 (m, 1H), 1.87-1.76 (m, 1H), 1.71 (dq, J=13.1, 6.6 Hz, 1H), 1.66-1.57 (m, 2H), 1.50 (ddd, J=14.1, 8.2, 5.9 Hz, 2H), 1.34-1.26 (m, 1H), 1.21 (s, 9H), 1.03 (d, J=6.4 Hz, 3H), 0.94 (d, J=6.5 Hz, 3H), 0.88 (d, J=6.5 Hz, 3H); MW: 731.8 g/mol; LC-MS m/z: 732.4

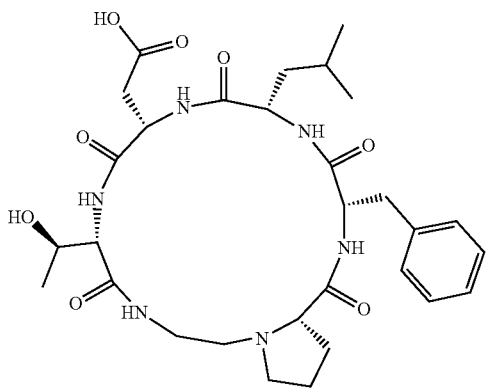 [SMILES: CC(C)C[C@@H]1NC(=O)[C@H](Cc2ccccc2)NC(=O)[C@@H]2CCCN2CCNC(=O)[C@H]([C@@H](C)O)NC(=O)[C@H](CC(=O)O)NC1=O]

Compound 39:

$^1$H NMR (500 MHz, DMSO-d$_6$) δ 8.78 (d, J=3.2 Hz, 1H), 8.58 (d, J=7.1 Hz, 1H), 7.81 (d, J=10.3 Hz, 1H), 7.72 (dd, J=7.4, 3.3 Hz, 1H), 7.43 (d, J=9.9 Hz, 1H), 7.30-7.22 (m, 4H), 7.22-7.12 (m, 1H), 4.99 (d, J=4.7 Hz, 1H), 4.69 (ddd, J=11.6, 10.3, 4.1 Hz, 1H), 4.33 (ddd, J=9.5, 7.1, 4.1 Hz, 1H), 4.29-4.22 (m, 1H), 4.13-4.04 (m, 1H), 3.88 (td, J=7.5, 3.2 Hz, 1H), 3.65 (dtd, J=12.4, 6.8, 2.5 Hz, 1H), 3.29 (dd, J=13.9, 4.1 Hz, 1H), 3.11 (ddd, J=8.6, 6.9, 1.8 Hz, 1H), 2.94-2.77 (m, 4H), 2.72 (dd, J=9.8, 5.4 Hz, 1H), 2.67-2.59 (m, 1H), 2.48-2.41 (m, 1H), 2.16-2.08 (m, 1H), 1.88-1.77 (m, 1H), 1.68-1.42 (m, 5H), 1.26-1.14 (m, 1H), 1.03 (d, J=6.4 Hz, 3H), 0.92 (d, J=6.3 Hz, 3H), 0.88 (d, J=6.4 Hz, 3H); MW: 616.7 g/mol; LC-MS m/z: 617.3

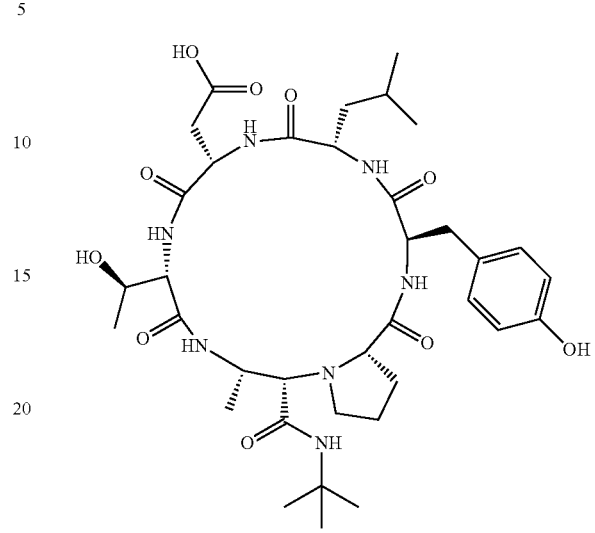

Compound 40:

1H NMR (700 MHz, DMSO-d$_6$) δ 9.02 (d, J=4.2 Hz, 1H), 8.43 (d, J=7.6 Hz, 1H), 7.46 (d, J=7.5 Hz, 1H), 7.03-6.97 (m, 2H), 6.82 (d, J=8.7 Hz, 1H), 6.75 (s, 1H), 6.69 (br s, 1H), 6.65-6.60 (m, 2H), 5.02 (s, 1H), 4.49 (q, J=7.5 Hz, 1H), 4.32-4.23 (m, 2H), 4.18 (td, J=6.4, 4.2 Hz, 1H), 4.04-3.94 (m, 1H), 3.88 (dd, J=8.7, 1.9 Hz, 1H), 3.34-3.28 (m, 1H), 3.11 (d, J=9.9 Hz, 1H), 3.01 (dd, J=14.4, 6.4 Hz, 1H), 2.89 (q, J=8.2 Hz, 1H), 2.80-2.68 (m, 4H), 1.77-1.69 (m, 1H), 1.69-1.58 (m, 4H), 1.53 (dtd, J=11.9, 9.2, 8.1, 6.0 Hz, 1H), 1.40 (dd, J=11.6, 9.5 Hz, 1H), 1.25 (s, 9H), 0.98 (dd, J=17.0, 6.5 Hz, 6H), 0.85 (dd, J=10.9, 6.0 Hz, 6H). $^{13}$C NMR (126 MHz, DMSO-d$_6$) δ 175.1, 174.9, 171.7, 171.4, 170.6, 169.2, 168.7, 156.1, 130.2, 128.6, 115.3, 65.5, 64.9, 64.6, 58.2, 53.9, 53.3, 51.0, 50.8, 45.7, 41.2, 40.9, 35.5, 34.0, 28.7, 28.6, 24.8, 24.0, 23.7, 21.3, 20.9, 19.2; MW: 745.9 g/mol; LC-MS m/z: 746.4

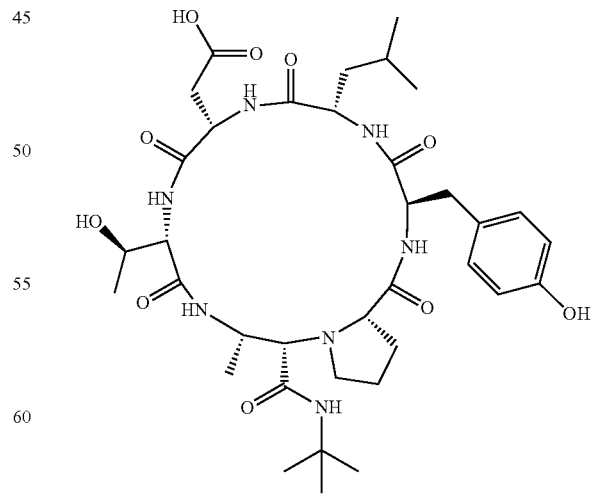

Compound 41:

1H NMR (500 MHz, DMSO-d6) δ 9.15 (br s, 1H), 8.43 (d, J=7.6 Hz, 1H), 7.54-7.44 (m, 1H), 7.08-6.97 (m, 2H), 6.92 (d, J=8.6 Hz, 1H), 6.76 (br s, 2H), 6.68-6.57 (m, 2H), 4.49 (q, J=7.6 Hz, 1H), 4.28 (tt, J=7.2, 4.2 Hz, 2H), 4.17 (d, J=4.9 Hz, 1H), 4.04-3.92 (m, 1H), 3.86 (dd, J=8.6, 2.0 Hz, 1H), 3.37-3.26 (m, 1H), 3.10 (d, J=9.9 Hz, 1H), 3.01 (dd, J=14.3, 6.2 Hz, 1H), 2.93 (q, J=8.1 Hz, 1H), 2.80-2.69 (m, 2H), 2.60 (d, J=7.2 Hz, 2H), 1.78-1.67 (m, 1H), 1.68-1.56 (m, 4H), 1.55-1.46 (m, 1H), 1.39 (dd, J=12.5, 9.9 Hz, 1H), 1.25 (s, 9H), 0.98 (dd, J=15.1, 6.4 Hz, 6H), 0.85 (dd, J=10.2, 6.2 Hz, 6H); MW: 745.9 g/mol; LC-MS m/z: 746.4

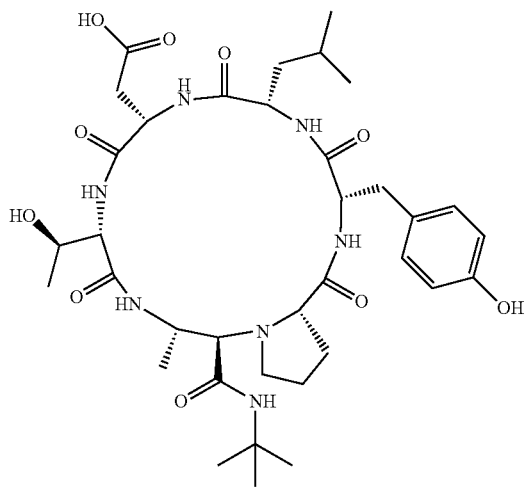 [SMILES: CC(C)C[C@@H]1NC(=O)[C@H](Cc2ccc(O)cc2)NC(=O)[C@@H]2CCCN2[C@@H](C(=O)NC(C)(C)C)[C@H](C)NC(=O)[C@H]([C@@H](C)O)NC(=O)[C@H](CC(=O)O)NC1=O]

Compound 42:

¹H NMR (500 MHz, DMSO-d₆) δ 8.69-8.60 (m, 1H), 8.50-8.39 (m, 1H), 8.13-8.06 (m, 1H), 7.79 (s, 1H), 7.45 (d, J=8.4 Hz, 1H), 7.35-7.26 (m, 1H), 7.01-6.89 (m, 2H), 6.62 (d, J=8.5 Hz, 2H), 4.80 (s, 1H), 4.40 (dt, J=8.2, 6.9 Hz, 1H), 4.27 (q, J=7.4 Hz, 1H), 4.17 (dd, J=9.0, 2.7 Hz, 1H), 3.95 (s, 1H), 3.90-3.79 (m, 2H), 3.67-3.56 (m, 1H), 3.50 (d, J=10.1 Hz, 1H), 2.97 (q, J=7.2, 4.9 Hz, 1H), 2.92-2.84 (m, 2H), 2.80 (t, J=6.6 Hz, 3H), 1.70 (dt, J=11.7, 8.8 Hz, 1H), 1.65-1.51 (m, 2H), 1.39 (td, J=15.2, 14.0, 7.4 Hz, 4H), 1.25 (s, 10H), 1.11 (d, J=6.4 Hz, 3H), 0.98 (d, J=6.3 Hz, 3H), 0.83 (d, J=5.8 Hz, 3H), 0.72 (d, J=5.4 Hz, 3H); MW: 745.9 g/mol; LC-MS m/z: 746.4

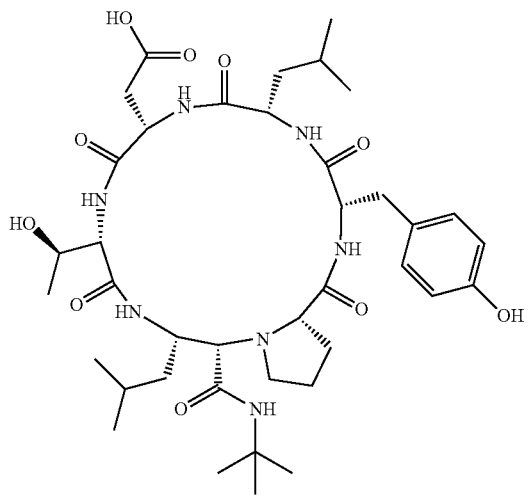 [SMILES: CC(C)C[C@@H]1NC(=O)[C@H](Cc2ccc(O)cc2)NC(=O)[C@@H]2CCCN2[C@H](C(=O)NC(C)(C)C)[C@H](CC(C)C)NC(=O)[C@H]([C@@H](C)O)NC(=O)[C@H](CC(=O)O)NC1=O]

Compound 43:

MW: 787.9 g/mol; LC-MS m/z: 788.5

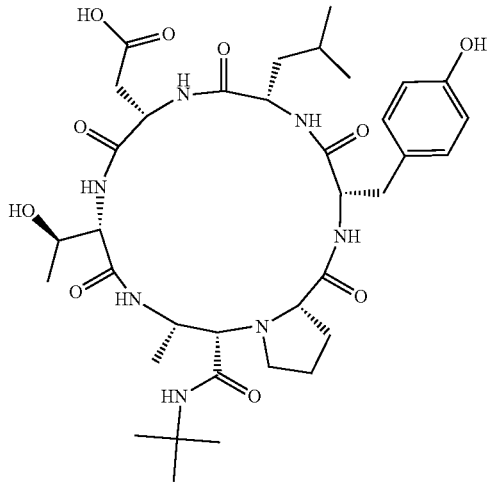 [SMILES: CC(C)C[C@@H]1NC(=O)[C@H](Cc2ccc(O)cc2)NC(=O)[C@@H]2CCCN2[C@H](C(=O)NC(C)(C)C)[C@H](C)NC(=O)[C@H]([C@@H](C)O)NC(=O)[C@H](CC(=O)O)NC1=O]

Compound 44:

¹H NMR (700 MHz, DMSO-d₆) δ 9.20 (s, 1H), 8.65 (d, J=4.5 Hz, 1H), 7.65 (d, J=6.6 Hz, 1H), 6.95-6.91 (m, 2H), 6.88 (d, J=9.0 Hz, 1H), 6.84 (dd, J=9.0, 7.5 Hz, 2H), 6.69-6.65 (m, 2H), 6.28 (s, 1H), 5.01 (s, 1H), 4.33-4.26 (m, 2H), 4.24 (dt, J=8.6, 4.3 Hz, 1H), 4.18-4.13 (m, 1H), 4.07-3.99 (m, 1H), 3.90 (dd, J=9.1, 1.6 Hz, 1H), 3.39 (q, J=8.0 Hz, 1H), 3.22 (d, J=10.7 Hz, 1H), 3.11 (dd, J=9.2, 5.8 Hz, 1H), 2.82 (ddd, J=10.4, 6.9, 2.3 Hz, 1H), 2.79-2.68 (m, 2H), 2.67-2.56 (m, 1H), 2.33-2.22 (m, 1H), 2.02-1.92 (m, 1H), 1.76-1.60 (m, 3H), 1.59-1.50 (m, 2H), 1.20 (s, 9H), 1.08 (d, J=6.5 Hz, 3H), 1.00 (d, J=6.5 Hz, 3H), 0.89 (d, J=6.6 Hz, 3H), 0.85 (d, J=6.5 Hz, 3H); MW: 759.9 g/mol; LC-MS m/z: 760.4

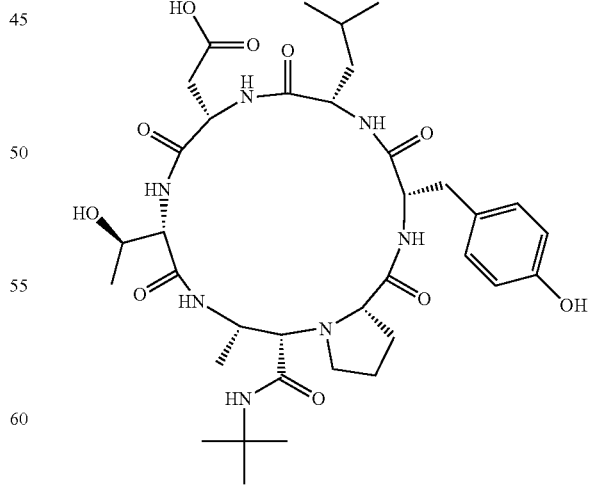

Compound 45:

MW: 759.9 g/mol; LC-MS m/z: 760.4

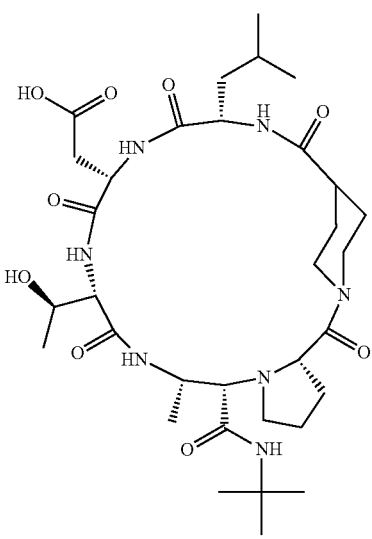 [SMILES: CC(C)C[C@@H]1NC(=O)C2CCN(CC2)C(=O)[C@@H]2CCCN2[C@H](C(=O)NC(C)(C)C)[C@H](C)NC(=O)[C@H]([C@@H](C)O)NC(=O)[C@H](CC(=O)O)NC1=O]
Compound 46:
MW: 693.8 g/mol; LC-MS m/z: 694.4
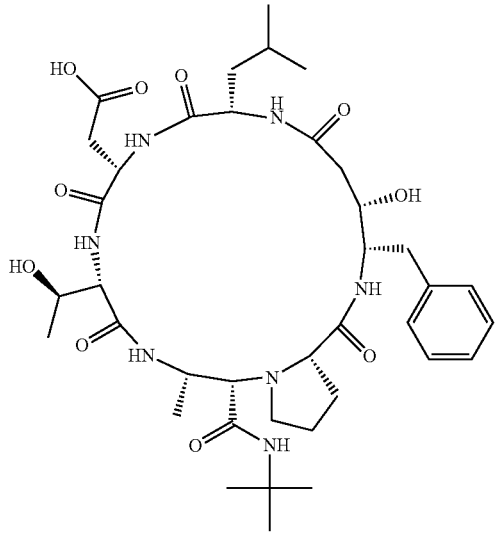 [SMILES: CC(C)C[C@@H]1NC(=O)C[C@H](O)[C@H](Cc2ccccc2)NC(=O)[C@@H]2CCCN2[C@H](C(=O)NC(C)(C)C)[C@H](C)NC(=O)[C@H]([C@@H](C)O)NC(=O)[C@H](CC(=O)O)NC1=O]
Compound 47:
MW: 773.9 g/mol; LC-MS m/z: 774.4
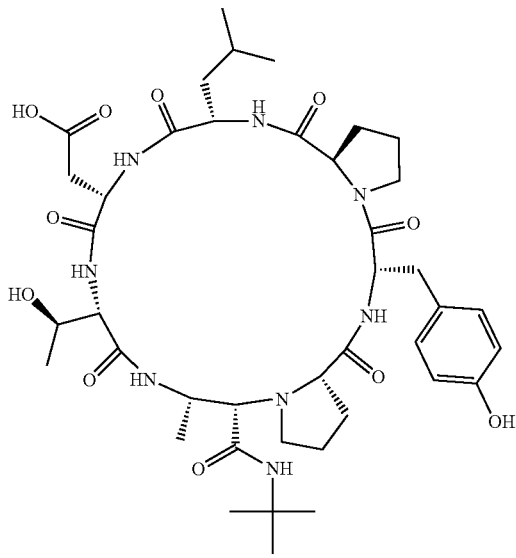 [SMILES: CC(C)C[C@@H]1NC(=O)[C@H]2CCCN2C(=O)[C@H](Cc2ccc(O)cc2)NC(=O)[C@@H]2CCCN2[C@H](C(=O)NC(C)(C)C)[C@H](C)NC(=O)[C@H]([C@@H](C)O)NC(=O)[C@H](CC(=O)O)NC1=O]
Compound 48:
$^1$H NMR (500 MHz, DMSO-d$_6$) δ 9.21 (br s, 1H), 7.95-7.82 (m, 2H), 6.99-6.91 (m, 2H), 6.88 (d, J=9.6 Hz, 1H), 6.80 (s, 1H), 6.71-6.59 (m, 3H), 5.18-5.07 (m, 1H), 4.80 (q, J=7.8 Hz, 1H), 4.73-4.63 (m, 1H), 4.56-4.50 (m, 1H), 4.38-4.28 (m, 2H), 4.28-4.20 (m, 1H), 3.82 (dd, J=9.0, 1.3 Hz, 1H), 3.35-3.32 (m, 2H), 3.03-2.58 (m, 7H), 2.25 (d, J=11.3 Hz, 1H), 1.91-1.79 (m, 1H), 1.72-1.44 (m, 10H), 1.28 (td, J=7.0, 0.8 Hz, 3H), 1.20 (s, 9H), 1.01 (d, J=6.4 Hz, 3H), 0.88 (dd, J=14.2, 6.5 Hz, 6H); MW: 843.0 g/mol; LC-MS m/z: 843.6
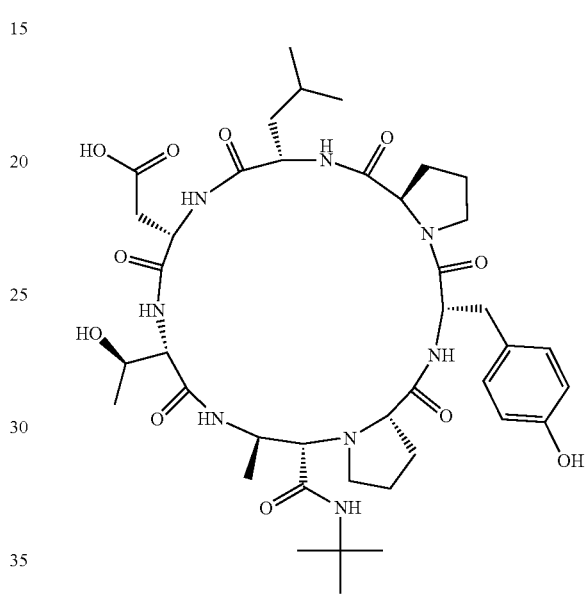
Compound 49:
MW: 843.0 g/mol; LC-MS m/z: 843.4
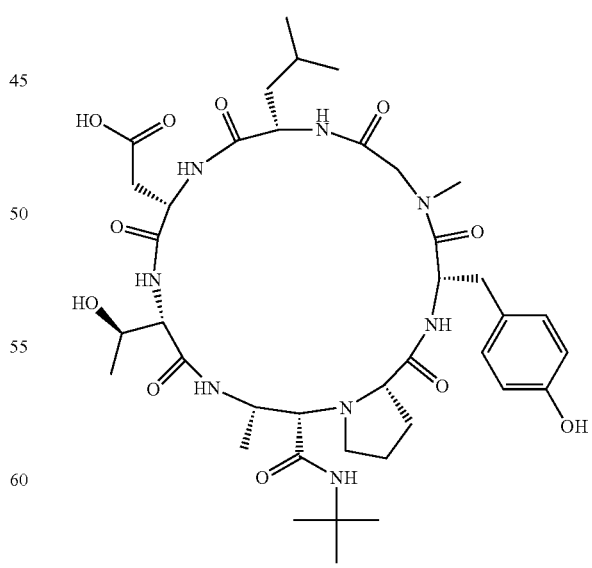
Compound 50:
MW: 816.9 g/mol; LC-MS m/z: 817.4

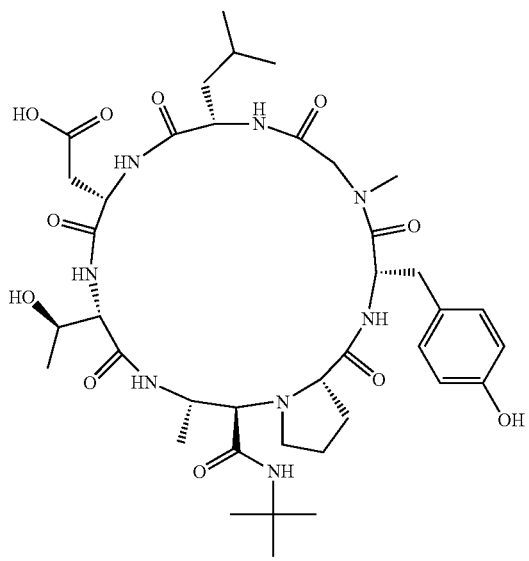 [SMILES: CC(C)C[C@@H]1NC(=O)CN(C)C(=O)[C@H](Cc2ccc(O)cc2)NC(=O)[C@@H]2CCCN2[C@@H](C(=O)NC(C)(C)C)[C@H](C)NC(=O)[C@H]([C@@H](C)O)NC(=O)[C@H](CC(=O)O)NC1=O]

Compound 51:

MW: 816.9 g/mol; LC-MS m/z: 817.4

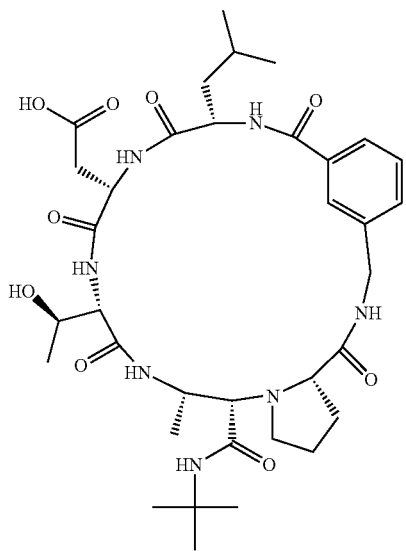 [SMILES: CC(C)C[C@@H]1NC(=O)c2cccc(c2)CNC(=O)[C@@H]2CCCN2[C@H](C(=O)NC(C)(C)C)[C@H](C)NC(=O)[C@H]([C@@H](C)O)NC(=O)[C@H](CC(=O)O)NC1=O]

Compound 52:

¹H NMR (700 MHz, DMSO-d₆) δ 8.95 (d, J=5.2 Hz, 1H), 8.21-8.15 (m, 1H), 8.02 (d, J=7.5 Hz, 1H), 7.65 (dd, J=7.4, 1.4 Hz, 2H), 7.46-7.43 (m, 1H), 7.40 (td, J=7.5, 0.9 Hz, 1H), 7.04 (s, 1H), 7.01 (d, J=9.3 Hz, 1H), 6.90 (d, J=9.1 Hz, 1H), 5.01 (s, 1H), 4.69-4.56 (m, 2H), 4.35 (dt, J=6.8, 5.6 Hz, 1H), 4.32-4.28 (m, 1H), 4.26-4.18 (m, 1H), 4.15 (dd, J=15.8, 5.2 Hz, 1H), 3.95 (dd, J=9.2, 1.8 Hz, 1H), 3.58-3.49 (m, 2H), 3.35-3.28 (m, 1H), 3.22 (d, J=10.6 Hz, 1H), 2.92 (ddd, J=8.9, 6.7, 2.6 Hz, 1H), 2.76 (d, J=6.3 Hz, 2H), 1.87 (tdd, J=12.6, 9.9, 7.0 Hz, 1H), 1.75-1.66 (m, 4H), 1.61 (qt, J=12.2, 10.7, 4.1 Hz, 2H), 1.26 (d, J=6.5 Hz, 3H), 1.20 (s, 9H), 0.99 (d, J=6.4 Hz, 3H), 0.94 (d, J=6.4 Hz, 3H), 0.86 (d, J=6.4 Hz, 3H); MW: 715.8 g/mol; LC-MS m/z: 716.3

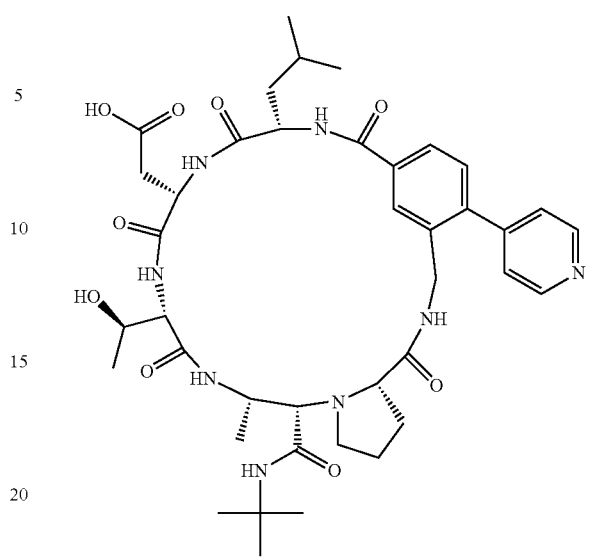

Compound 53:

¹H NMR (700 MHz, DMSO-d₆) δ 12.54 (s, 1H), 8.95 (d, J=5.2 Hz, 1H), 8.73-8.65 (m, 2H), 8.18 (t, J=6.5 Hz, 1H), 8.17-8.11 (m, 1H), 7.84-7.74 (m, 2H), 7.50-7.43 (m, 2H), 7.37 (d, J=7.8 Hz, 1H), 7.01 (s, 1H), 6.98 (d, J=9.3 Hz, 1H), 6.92 (d, J=9.1 Hz, 1H), 5.03 (d, J=4.5 Hz, 1H), 4.62 (ddd, J=11.3, 7.2, 3.7 Hz, 1H), 4.51 (dd, J=15.8, 7.3 Hz, 1H), 4.42-4.35 (m, 1H), 4.30 (ddd, J=6.5, 4.5, 1.7 Hz, 1H), 4.22 (ddd, J=10.7, 9.4, 6.5 Hz, 1H), 4.11 (dd, J=15.9, 5.5 Hz, 1H), 3.96 (dd, J=9.2, 1.7 Hz, 1H), 3.57-3.50 (m, 2H), 3.25 (d, J=10.6 Hz, 1H), 2.91 (ddd, J=8.9, 6.7, 2.5 Hz, 1H), 2.78 (d, J=6.3 Hz, 2H), 1.83 (ddt, J=9.8, 5.4, 2.3 Hz, 1H), 1.78-1.70 (m, 2H), 1.70-1.60 (m, 3H), 1.54 (dddd, J=15.8, 11.4, 6.0, 4.0 Hz, 1H), 1.29 (d, J=6.5 Hz, 3H), 1.21 (s, 9H), 0.98 (d, J=6.4 Hz, 3H), 0.95 (d, J=6.5 Hz, 3H), 0.88 (d, J=6.5 Hz, 3H). ¹³C NMR (126 MHz, DMSO-d₆) δ 175.01, 174.93, 171.83, 170.18, 169.86, 169.03, 167.29, 150.18, 147.53, 140.74, 137.41, 134.85, 129.82, 126.64, 126.35, 124.45, 67.57, 65.63, 64.91, 57.77, 52.59, 51.95, 50.87, 46.53, 45.44, 41.67, 35.66, 31.20, 28.65, 24.82, 24.69, 23.76, 21.40, 20.86, 20.47; MW: 792.9 g/mol; LC-MS m/z: 793.4

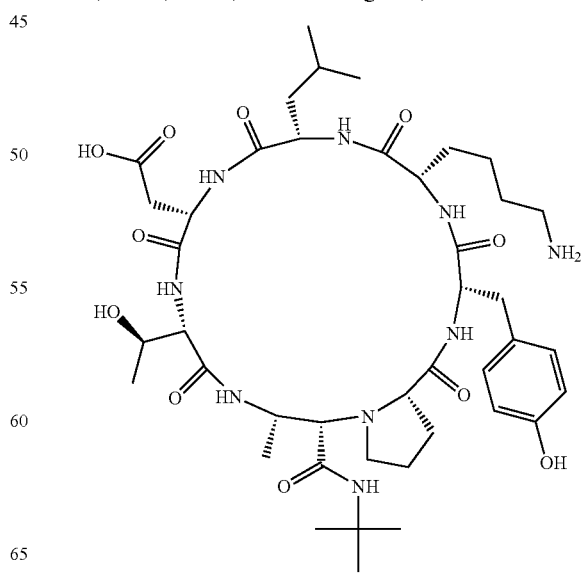

Compound 54:

MW: 888.1 g/mol; LC-MS m/z: 888.4

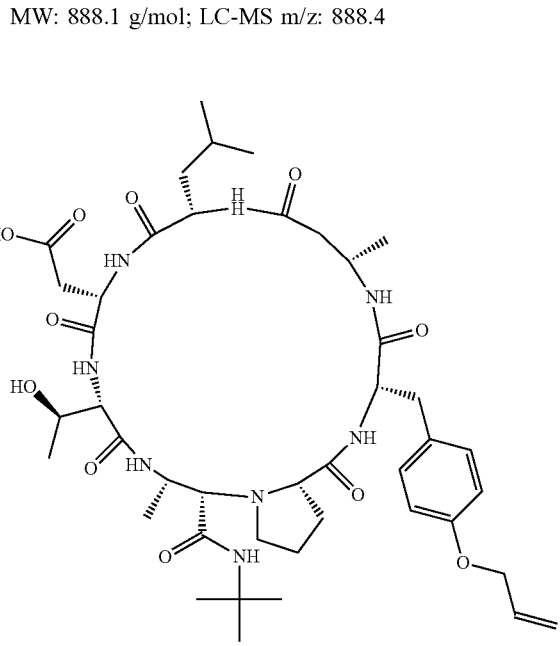

Compound 55:

MW: 871.0 g/mol; LC-MS m/z: 871.5

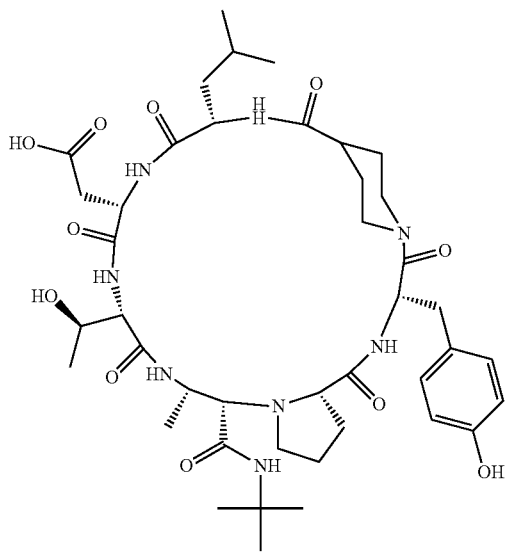

Compound 56:

MW: 857.0 g/mol; LC-MS m/z: 857.4

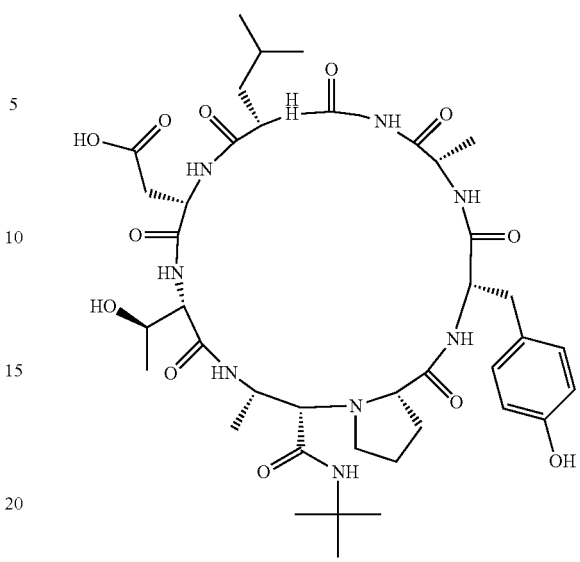

Compound 57:
$^1$H NMR (500 MHz, DMSO-d$_6$) δ9.36 (br s, 1H), 8.84-8.66 (m, 1H), 8.44 (d, J=6.5 Hz, 1H), 7.59-7.35 (m, 2H), 7.02-6.87 (m, 2H), 6.89-6.83 (m, 1H), 6.68-6.60 (m, 2H), 6.62-6.54 (m, 2H), 5.16 (br s, 1H), 4.56-4.48 (m, 1H), 4.44 (q, J=7.1 Hz, 1H), 4.35-4.24 (m, 2H), 4.11-4.02 (m, 1H), 3.92-3.77 (m, 2H), 3.48 (d, J=7.8 Hz, 1H), 3.39 (d, J=5.4 Hz, 1H), 3.25 (dd, J=9.6, 3.0 Hz, 1H), 3.02 (d, J=10.8 Hz, 1H), 2.90 (dd, J=13.9, 5.3 Hz, 1H), 2.72 (t, J=7.6 Hz, 1H), 2.69-2.59 (m, 3H), 1.79 (dq, J=16.3, 11.0, 10.5 Hz, 2H), 1.74-1.62 (m, 1H), 1.63-1.47 (m, 3H), 1.39-1.29 (m, 1H), 1.26 (d, J=7.0 Hz, 3H), 1.21 (s, 9H), 1.12 (d, J=6.4 Hz, 3H), 1.03 (d, J=6.4 Hz, 3H), 0.84 (dd, J=6.6, 2.1 Hz, 6H); MW: 874.0 g/mol; LC-MS m/z: 874.4

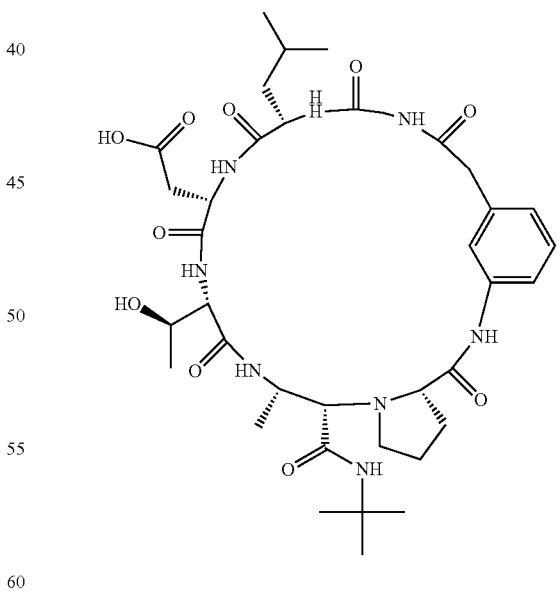

Compound 58:
MW: 772.9 g/mol; LC-MS m/z: 773.5

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

The invention claimed is:

1. A cyclic peptide of formula (II):

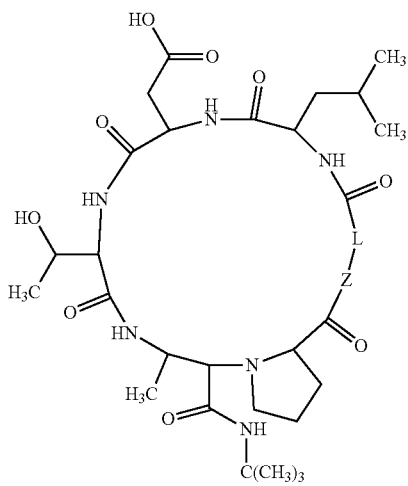

(II)

or a stereoisomer thereof,
wherein:
—C(O)-L-Z— is selected from the group consisting of:

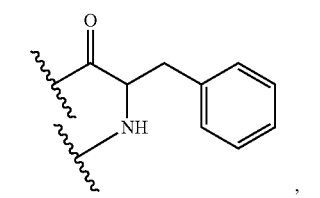

(a)

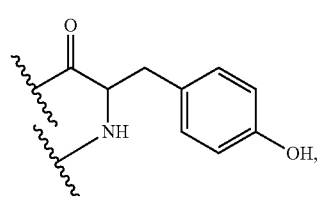

(b)

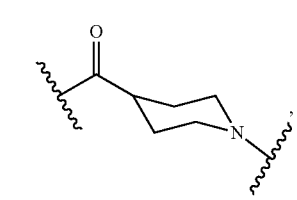

(c)

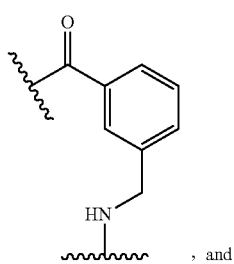

(d)

, and

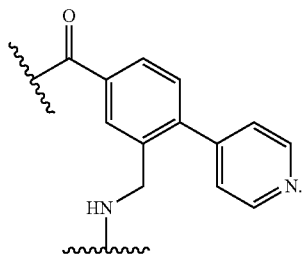

(e)

2. The cyclic peptide of claim 1, or a stereoisomer thereof, wherein —C(O)-L-Z— is:

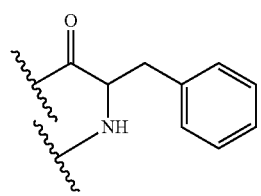

(a)

3. The cyclic peptide of claim 2, or a stereoisomer thereof, wherein the cyclic peptide, or stereoisomer thereof, is:

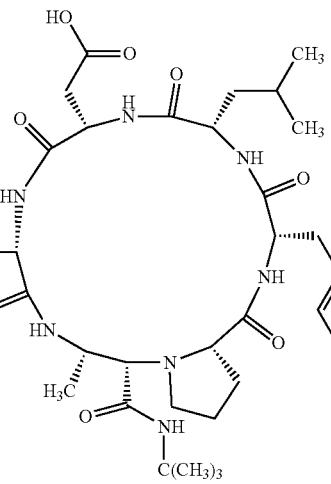

4. The cyclic peptide of claim 1, or a stereoisomer thereof, wherein —C(O)-L-Z— is:

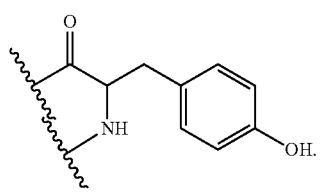

(b)

5. The cyclic peptide of claim 4, or a stereoisomer thereof, wherein the cyclic peptide, or stereoisomer thereof, is selected from the group consisting of:

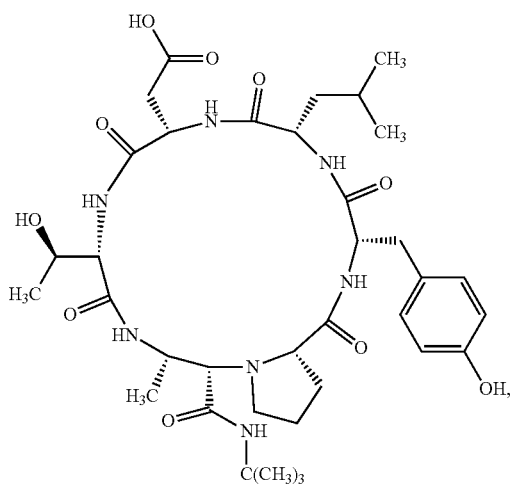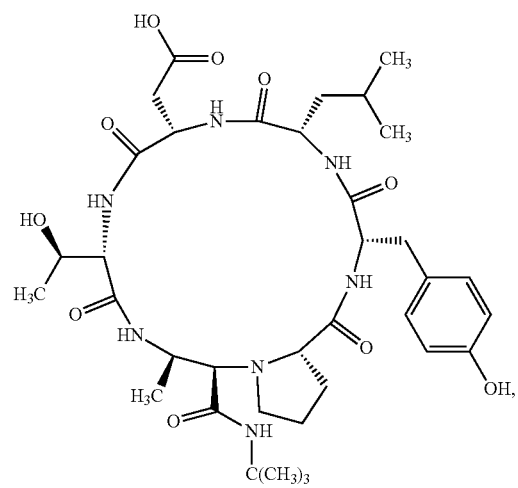
-continued
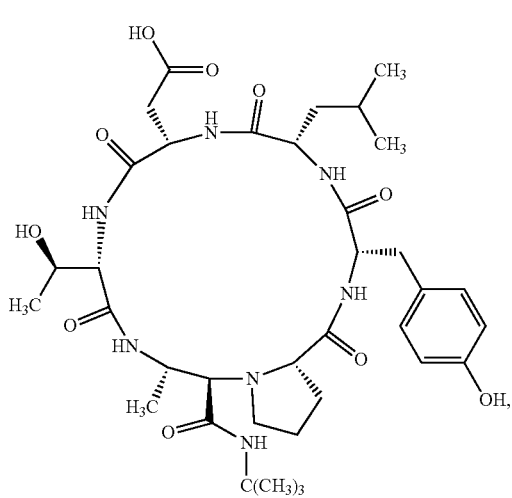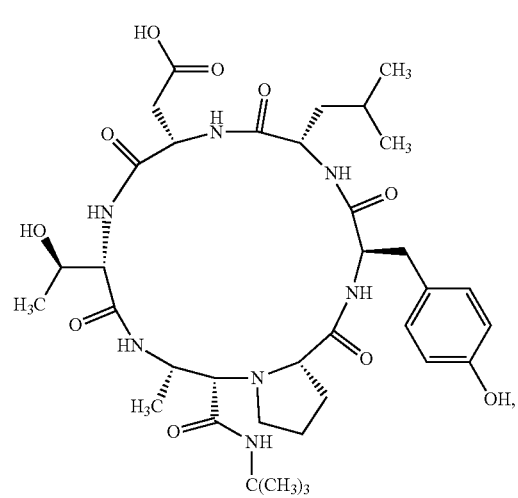 [SMILES: CC(C)C[C@@H]1NC(=O)[C@@H](Cc2ccc(O)cc2)NC(=O)[C@@H]2CCCN2[C@@H](C(=O)NC(C)(C)C)[C@H](C)NC(=O)[C@H]([C@@H](C)O)NC(=O)[C@H](CC(=O)O)NC1=O]
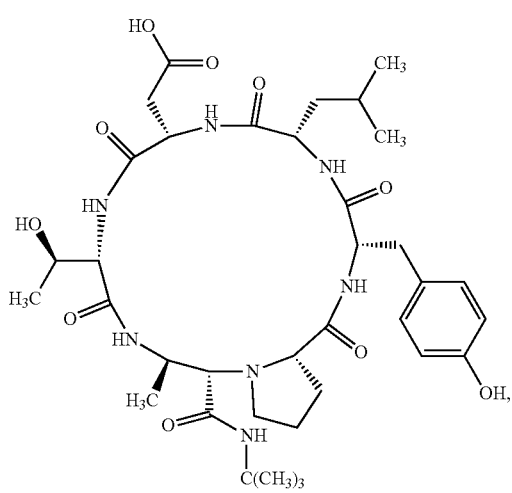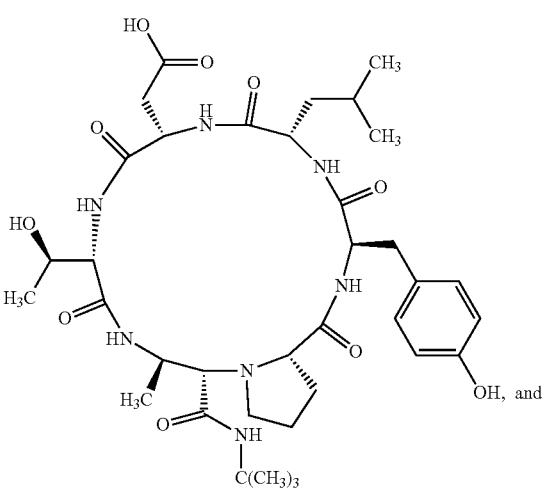

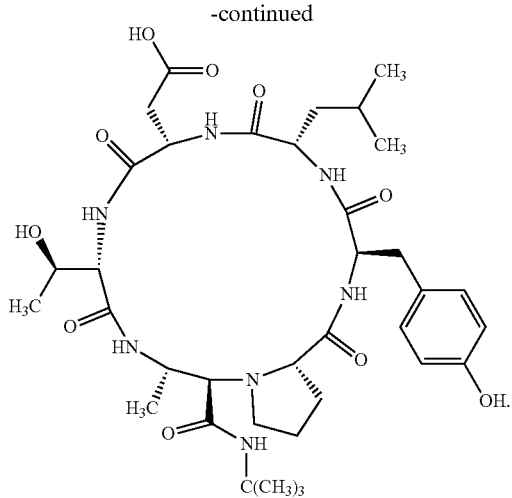

6. The cyclic peptide of claim 1, or a stereoisomer thereof, wherein —C(O)-L-Z— is:

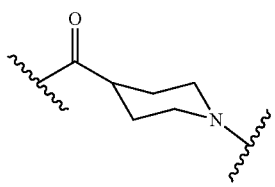

(c)

7. The cyclic peptide of claim 6, or a stereoisomer thereof, wherein the cyclic peptide, or stereoisomer thereof, is:

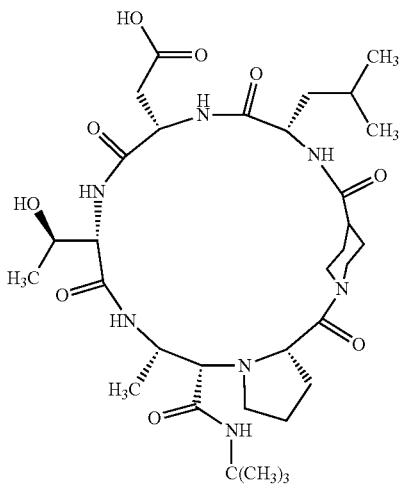

8. The cyclic peptide of claim 1, or a stereoisomer thereof, wherein —C(O)-L-Z— is:

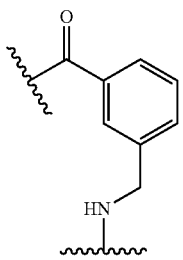

(d)

9. The cyclic peptide of claim 8, or a stereoisomer thereof, wherein the cyclic peptide, or stereoisomer thereof, is:

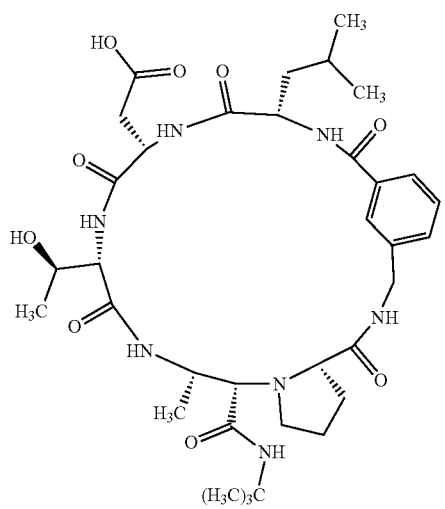

10. The cyclic peptide of claim 1, or a stereoisomer thereof, wherein —C(O)-L-Z— is:

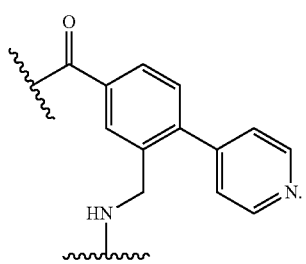

(e)

11. The cyclic peptide of claim 10, or a stereoisomer thereof, wherein the cyclic peptide, or stereoisomer thereof, is:

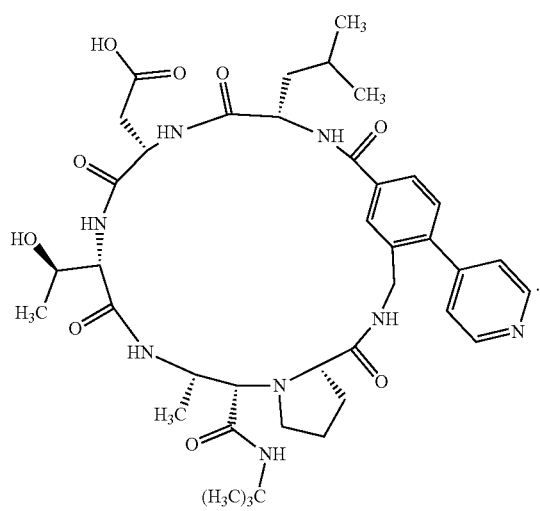
12. A cyclic peptide, or a stereoisomer thereof, wherein the cyclic peptide, or stereoisomer thereof, is selected from the group consisting of:
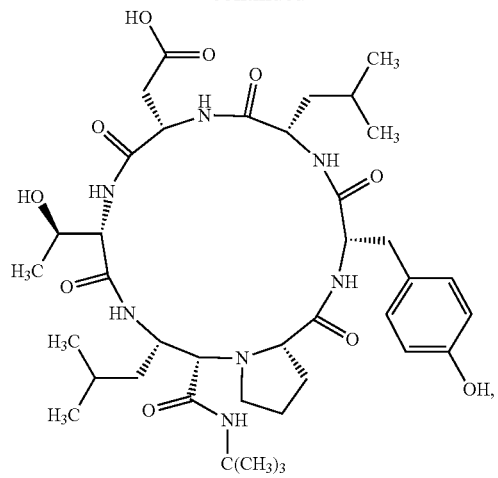
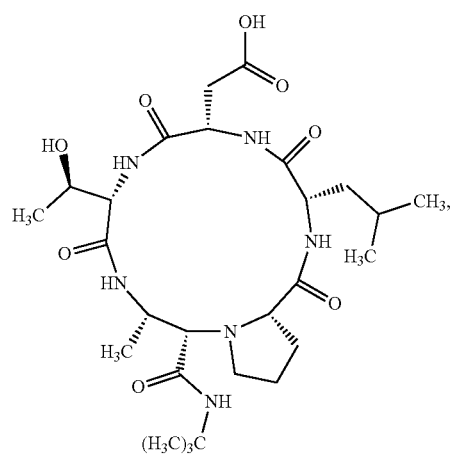
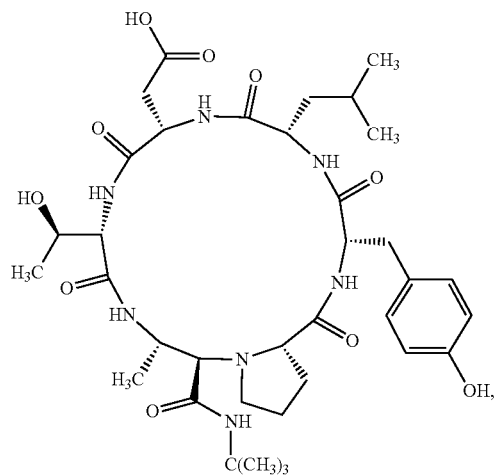
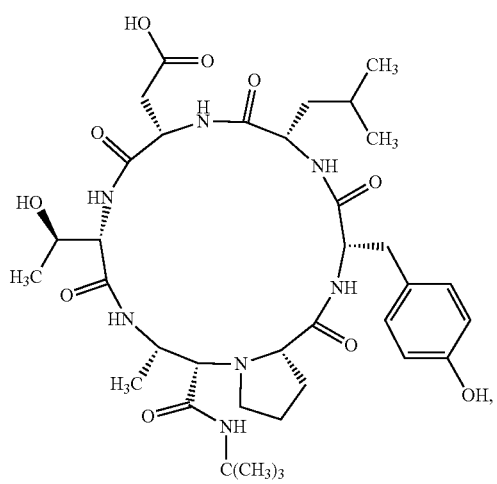
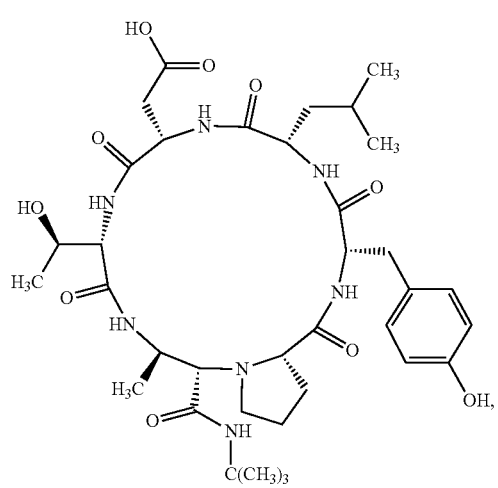

57
-continued
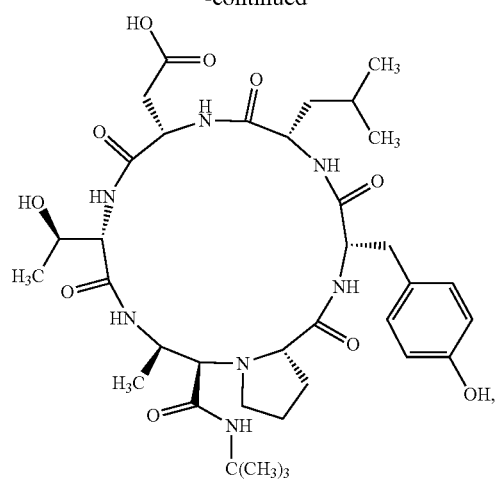
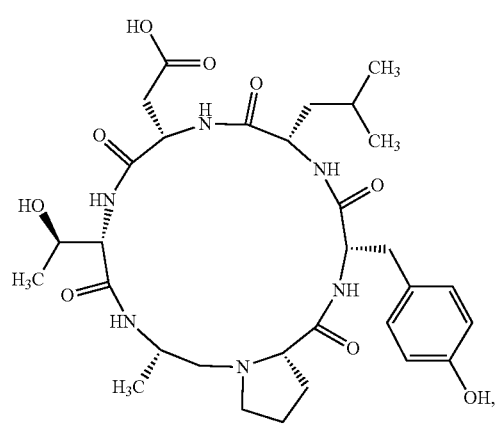
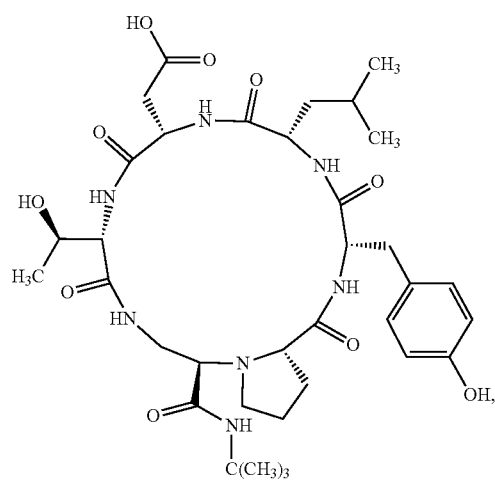
58
-continued
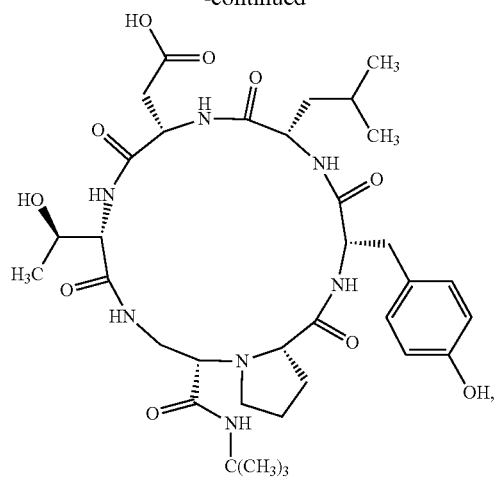
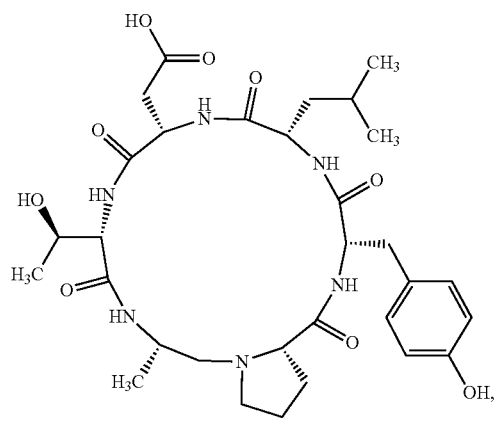
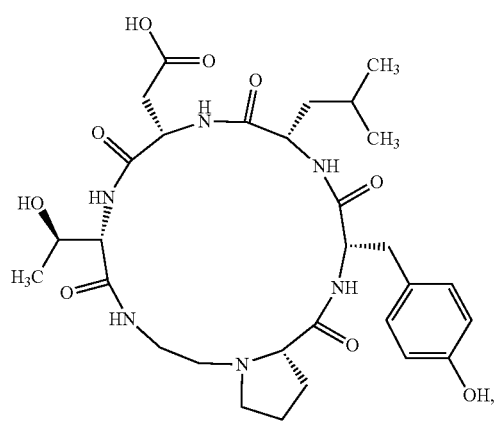

59
-continued
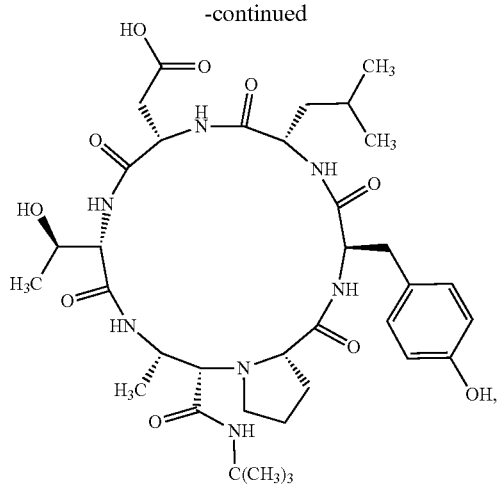
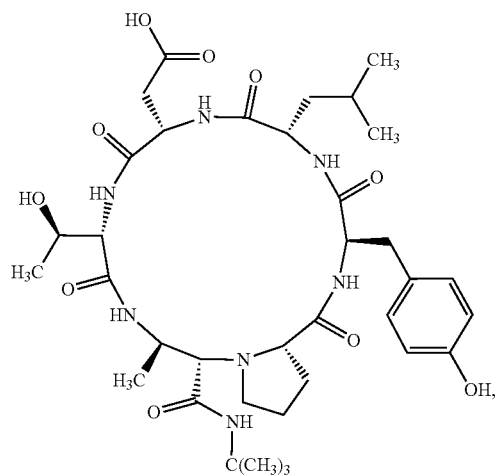
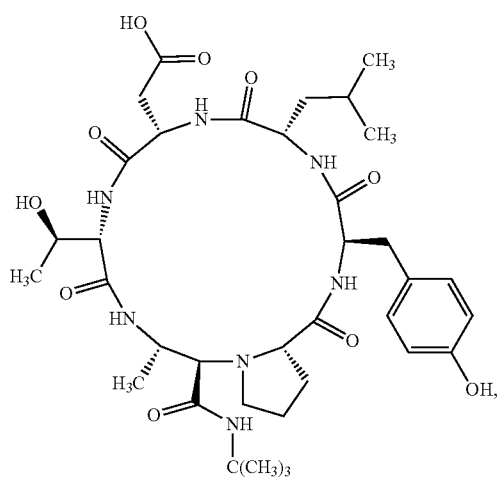
60
-continued
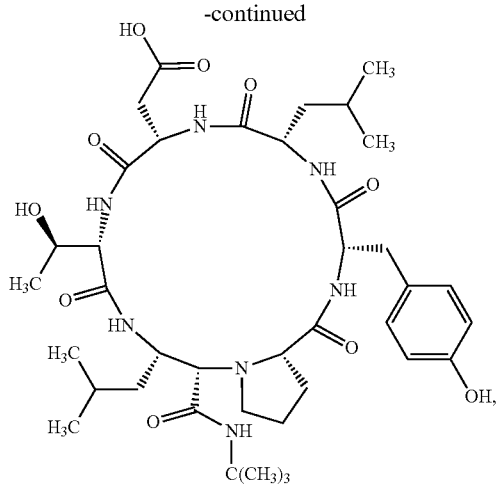
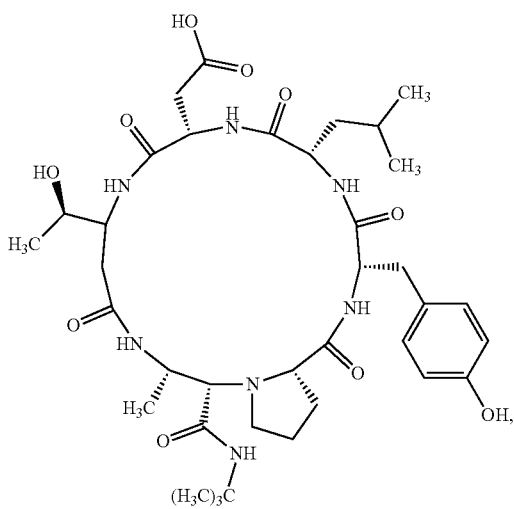
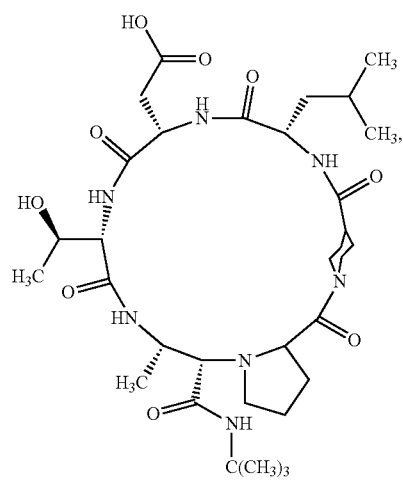

-continued
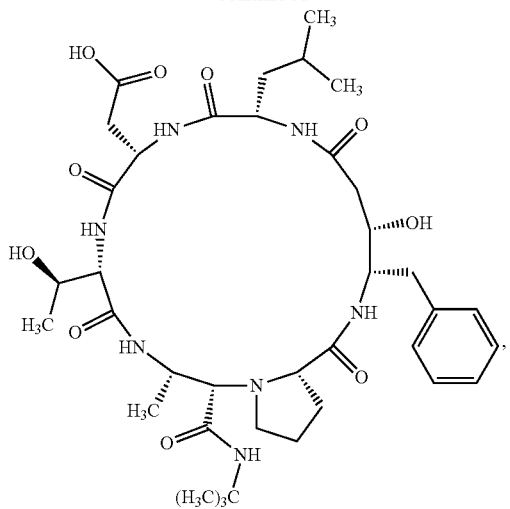
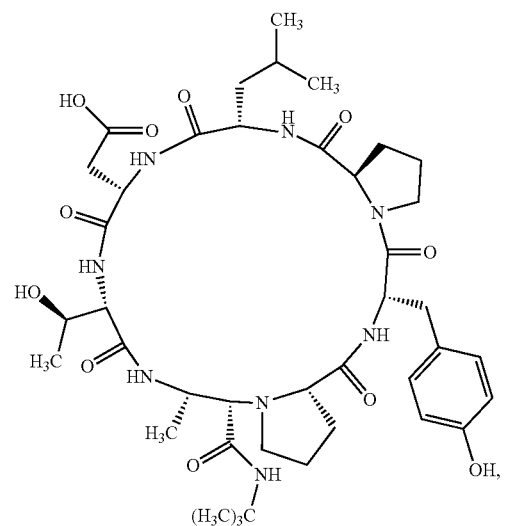
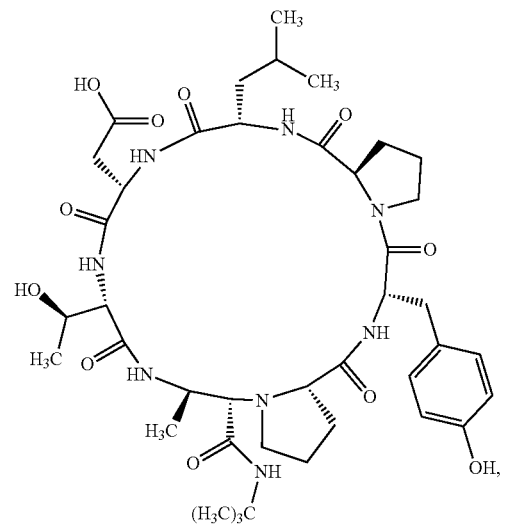
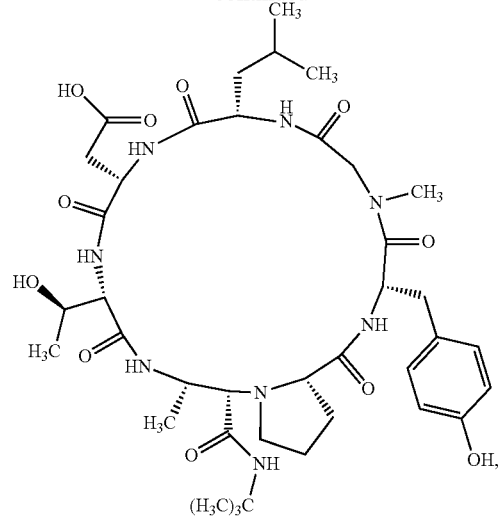
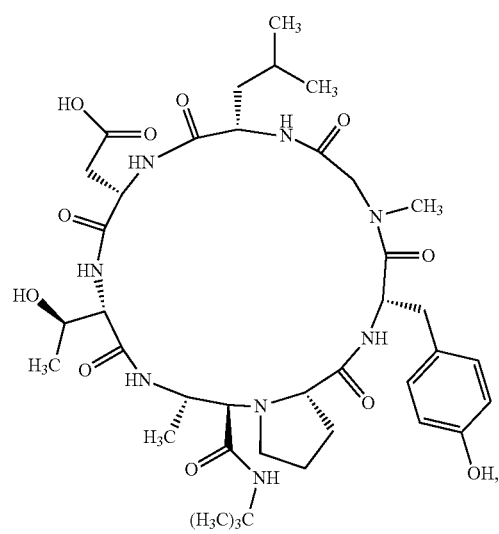
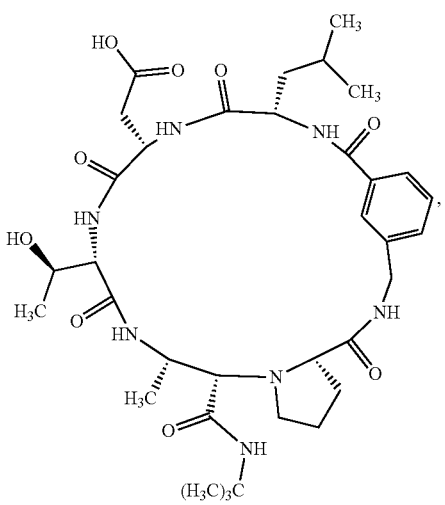

63
-continued
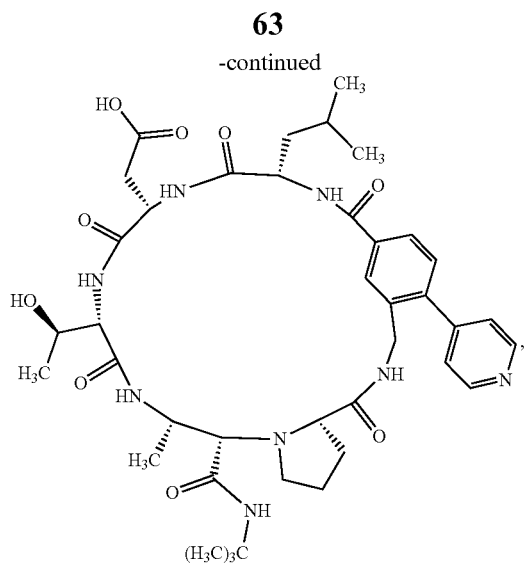
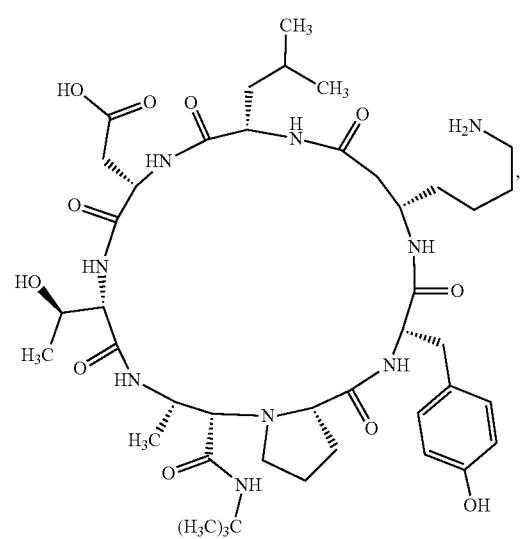
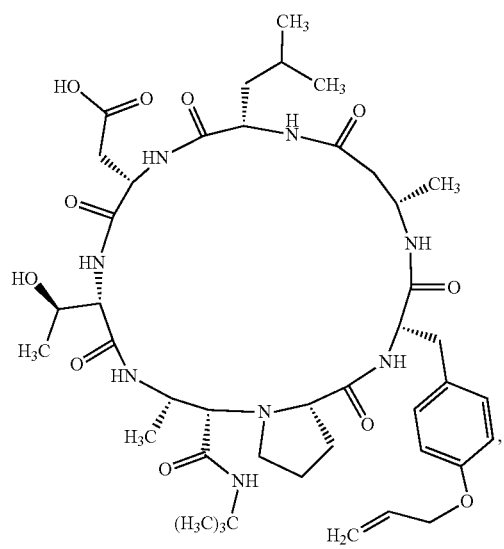
64
-continued
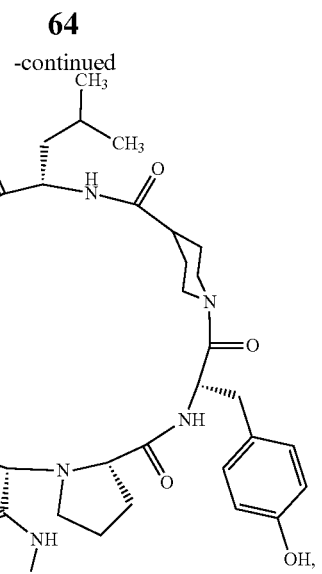
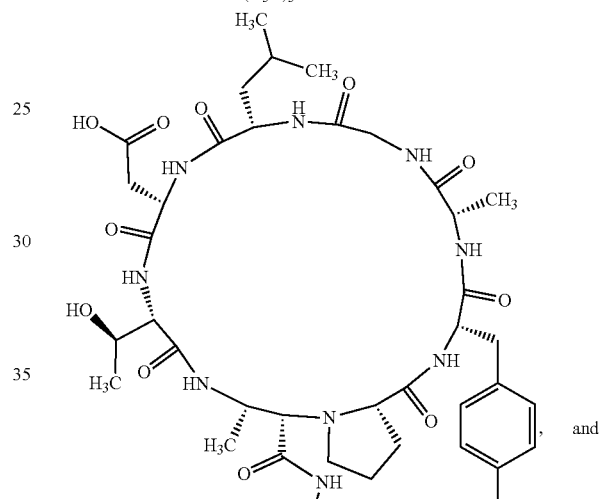
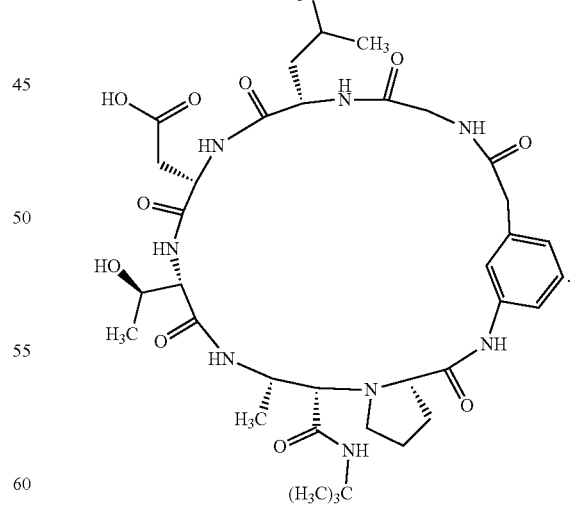
* * * * *

UNITED STATES PATENT AND TRADEMARK OFFICE
CERTIFICATE OF CORRECTION

PATENT NO. : 10,981,921 B2
APPLICATION NO. : 16/985096
DATED : April 20, 2021
INVENTOR(S) : Manuel Perez Vazquez et al.

It is certified that error appears in the above-identified patent and that said Letters Patent is hereby corrected as shown below:

In the Specification

Column 9, Line 37, replace "HC1." with –HCl–;
Line 57, replace "peptidomimetic" with –peptidomimetic.–.

Column 13, Line 28, replace ".HC1" with –HCl–;
Line 33, replace "HC1" with –HCl–;
Line 35, replace "HC1" with –HCl–.

Column 15, Line 48, replace "HC1" with –HCl–.

Column 17, Line 33, replace "CH$_2$C1$_2$" with –CH$_2$Cl$_2$–;
Line 40, replace "CH$_2$C1$_2$" with –CH$_2$Cl$_2$–.

Column 18, Line 3, replace "H-L-Pro-OBn.HC1" with –H-L-Pro-OBn·HCl–;
Line 34, replace "H-L-Pro-O'Bu.HC1" with –H-L-Pro-O'Bn·HCl–;
Line 40, replace "CH$_2$C1$_2$" with –CH$_2$Cl$_2$–;
Line 64, replace "H-L-Pro-OBn.HC1" with –H-L-Pro-OBn·HCl–.

Column 19, Line 25, replace "HC1" with –HCl–;
Line 28, replace "CH$_2$C1$_2$" with –CH$_2$Cl$_2$–;
Line 57, replace "CH$_2$C1$_2$" with –CH$_2$Cl$_2$–;
Line 58, replace "H-L-Pro-OBn.HC1" with –H-L-Pro-OBn·HCl–.

Column 20, Line 26, replace "N,O-dimethylhydroxylamine.HC1" with –N,O-dimethylhydroxylamine HCl–;
Line 31, replace "HC1" with –HCl–;
Line 60, replace "N HC1" with –N HCl–.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,981,921 B2

Column 21, Line 55, replace " $\xrightarrow{\text{LiOH} \quad \text{LiCl}}$ " with – $\xrightarrow{\text{LiOH} \quad \text{LiCl}}$ –.

Column 22, Line 7, replace "N HC1" with –N HCl–.

Column 23, Line 28, replace "N HC1" with –N HCl–.

Column 25, Line 44, replace "2-C1" with –2-Cl–;
        Line 51, replace "2-C1" with –2-Cl–;
        Line 56, replace "2-C1" with –2-Cl–.